(12) United States Patent
Jian et al.

(10) Patent No.: US 11,994,490 B2
(45) Date of Patent: *May 28, 2024

(54) ELECTROCHEMICAL GAS SENSOR ASSEMBLY

(71) Applicant: Honeywell International Inc., Charlotte, NC (US)

(72) Inventors: Johnny Jian, Shanghai (CN); Neils Hansen, Poole (GB); Keith Francis Edwin Pratt, Portsmouth (GB); Paul Westmarland, Surrey (GB); Fuxia Liu, Shanghai (CN)

(73) Assignee: Honeywell International Inc., Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/165,712

(22) Filed: Feb. 7, 2023

(65) Prior Publication Data
US 2023/0194461 A1     Jun. 22, 2023

Related U.S. Application Data

(63) Continuation of application No. 16/717,506, filed on Dec. 17, 2019, now Pat. No. 11,598,745.

(30) Foreign Application Priority Data

Dec. 29, 2018   (CN) .......................... 201811634269.X

(51) Int. Cl.
    *G01N 27/404*   (2006.01)
    *G01N 27/40*    (2006.01)
    (Continued)

(52) U.S. Cl.
    CPC ........... *G01N 27/404* (2013.01); *G01N 27/40* (2013.01); *G01N 27/413* (2013.01); *G01N 27/4078* (2013.01)

(58) Field of Classification Search
    CPC ............ G01N 27/404; G01N 27/4035; G01N 27/4071; G01N 27/4072; G01N 27/4078; G01N 27/40; G01N 27/413
    See application file for complete search history.

(56) References Cited

U.S. PATENT DOCUMENTS

5,930,337 A     7/1999  Mohler
8,888,978 B2    11/2014 Mitchell et al.
(Continued)

FOREIGN PATENT DOCUMENTS

CN    102597761 A    7/2012
CN    102735738 A    10/2012
(Continued)

OTHER PUBLICATIONS

Online Merriam-Webster defintions of "cap". downloaded Feb. 16, 2022 (Year: 2022).*

(Continued)

*Primary Examiner* — Alexander S Noguerola
(74) *Attorney, Agent, or Firm* — Alston & Bird LLP

(57) ABSTRACT

Various example embodiments described herein relate to an electrochemical gas sensor. The electrochemical gas sensor can include a sensor cap having one or more solid features disposed on a surface of the sensor cap. The electrochemical gas sensor can include a counter electrode configured to generate a gas during use of the electrochemical gas sensor. The electrochemical gas sensor can include a vent assembly adapted to release at least a portion of the gas generated at the counter electrode out from the electrochemical gas sensor. The vent assembly can include a vent conduit and a vent membrane that defines a passage for the gas to flow from an extended portion of the counter electrode, to the vent conduit, via the vent membrane, so as to be vented from the electrochemical gas sensor.

19 Claims, 7 Drawing Sheets

(51) Int. Cl.
  *G01N 27/413* (2006.01)
  *G01N 27/407* (2006.01)

(56) References Cited

U.S. PATENT DOCUMENTS

| | | | |
|---|---|---|---|
| 11,598,745 B2* | 3/2023 | Jian | G01N 27/40 |
| 2010/0170795 A1* | 7/2010 | Cowburn | G01N 27/404 |
| | | | 204/406 |
| 2011/0100814 A1 | 5/2011 | Brown et al. | |
| 2012/0018303 A1 | 1/2012 | Bordo et al. | |
| 2012/0228140 A1 | 9/2012 | Westmarland et al. | |
| 2015/0122649 A1 | 5/2015 | Westmarland et al. | |
| 2018/0143158 A1* | 5/2018 | Harris | G01N 27/404 |
| 2018/0266981 A1 | 9/2018 | Hansen | |

FOREIGN PATENT DOCUMENTS

| | | |
|---|---|---|
| CN | 104634835 A | 5/2015 |
| CN | 108027340 A | 5/2018 |
| DE | 102014007135 A | 11/2015 |
| WO | 2004/031758 A1 | 4/2004 |
| WO | 2007/115801 A1 | 10/2007 |
| WO | 2017/034535 A1 | 3/2017 |
| WO | 2017/155801 A1 | 9/2017 |

OTHER PUBLICATIONS

U.S. Appl. No. 16/717,506, filed Dec. 17, 2019.
CN Office Action, including Search Report Mailed on Aug. 26, 2023 for CN Application No. 201811634269, 16 page(s).
Decision to grant a European patent Mailed on Mar. 16, 2023 for EP Application No. 19219942, 2 page(s).
English Translation of CN Office Action, including Search Report dated Aug. 26, 2023 for CN Application No. 201811634269, 7 page(s).
Extended European Search Report for European Patent Application No. 19219942.0, dated Apr. 22, 2020, 10 pages.
Extended European Search Report Mailed on Apr. 26, 2023 for EP Application No. 23156168, 8 page(s).
Intention to grant Mailed on Nov. 4, 2022 for EP Application No. 19219942.
Non-Final Rejection Mailed on Feb. 24, 2022 for U.S. Appl. No. 16/717,506.
Notice of Allowance and Fees Due (PTOL-85) Mailed on Dec. 7, 2022 for U.S. Appl. No. 16/717,506.
Notice of Allowance and Fees Due (PTOL-85) Mailed on Jun. 10, 2022 for U.S. Appl. No. 16/717,506.
Notice of Allowance and Fees Due (PTOL-85) Mailed on Nov. 7, 2022 for U.S. Appl. No. 16/717,506.

* cited by examiner

ELECTROCHEMICAL GAS SENSOR ASSEMBLY

TECHNOLOGICAL FIELD

This application is a continuation application of U.S. patent application Ser. No. 16/717,506, filed Dec. 17, 2019, titled "Electrochemical Gas Sensor Assembly," which claims priority to and the benefit of Chinese Patent Application No. 201811634269.X, filed Dec. 29, 2018, titled "Electrochemical Gas Sensor Assembly," the entire contents of which are hereby incorporated by reference in their entirety for all purposes.

TECHNOLOGICAL FIELD

The present disclosure relates generally to, an electrochemical gas sensor assembly and, more particularly, to a structure of an electrochemical gas sensor, and systems, apparatuses, and methods associated therewith.

BACKGROUND

Gas monitoring systems are commonly installed in workplaces and other premises, to monitor concertation of various gases present in a working environment. Such gas monitoring systems, are often commonly referred as gas analyzers, gas detectors, gas sensors, or the like. One such type of the gas sensor is an electrochemical gas sensor. Electrochemical gas sensors can be used to detect various types of gases, such as oxygen as well as toxic gases including, but not limited to, carbon monoxide, sulphur dioxide, hydrogen sulfide, and the like. While existing electrochemical gas sensors often achieve reduced detection limits and improved selectivity at relatively low manufacturing costs, there is an ongoing desire in the industry for electrochemical sensors that are more robust and that avoid the many pitfalls of existing electrochemical sensors.

Applicant has identified a number of deficiencies and problems associated with existing electrochemical gas sensors having vents that release gases generated during operation. Through applied effort, ingenuity, and innovation, many of these identified problems have been solved by developing solutions that are included in embodiments of the present disclosure, many examples of which are described in detail herein.

SUMMARY

Various example embodiments described herein relates to, an electrochemical gas sensor (EGS) including a sensor cap, a counter electrode, and a vent assembly. In some embodiments, the sensor cap of the EGS includes one or more solid features defined on a surface of the sensor cap. Further, in accordance with said example embodiments, the counter electrode of the EGS can be adapted to generate a gas during use of the EGS and the vent assembly of the EGS can be adapted to release at least a portion of the gas generated at the counter electrode out of the EGS.

In an aspect, according to some example embodiments, the vent assembly of the EGS includes a vent conduit and a vent membrane. In this regard, the vent conduit can be defined by an aperture from an outside surface of the sensor cap, through the sensor cap, to a portion of an inner surface of the sensor cap. In this regard, the portion of the inner surface of the sensor cap corresponds to a portion of the vent membrane. The sensor cap, according to various example embodiments described herein, can be adapted to be positioned at a top end of the EGS.

In another aspect, according to some example embodiments, the vent membrane can be positioned over the counter electrode so that a portion of the vent membrane overlaps with an extended portion of the counter electrode, thereby defining a passage. In this regard, the passage defined can be operable so that any oxygen generated at the counter electrode, may be caused or allowed to flow through the extended portion into the vent membrane, and further vent out through the sensor cap of the EGS, via the vent conduit.

In another aspect, in accordance with various embodiments described herein, the one or more solid features on the sensor cap defines a cavity. The cavity can be defined between an internal surface of the one or more solid features and the vent membrane. In this regard, the cavity can be operable to accumulate at least a portion of the gas released out through the vent membrane before the portion of the gas eventually vents through the vent conduit.

According to some example embodiments, a gas sensor cap for an EGS can include a housing. In this aspect, a portion of the housing can include an aperture defined through at least one surface of the housing. In this aspect, the aperture through the at least one surface of the housing can be dimensioned and configured to prevent an ingress of water to the EGS and allow egress of gases from the EGS. Without wishing to be bound by any particular theory, the aperture of the sensor cap may be dimensioned and configured such that water can be prevented from ingress to the EGS at least partially due to capillarity. The housing of the sensor cap further includes one or more solid features disposed on the at least one surface of the portion of the housing. In this aspect, the one or more solid features are configured and dimensioned to prevent a deformation of a vent membrane during an assembly and use of the EGS with the gas sensor cap.

In an aspect, according to said example embodiment, the gas sensor cap can be adapted to be engaged at a top end of the EGS such that, the aperture of the sensor cap can be in fluidic communication with a portion of the EGS including a counter electrode. Further, according to said example embodiment, upon engagement with the EGS, the gas sensor cap can be adapted to vent out gas generated inside the EGS through a top end of the gas sensor cap.

In accordance with another example embodiment, an electrochemical oxygen sensor can be described. The electrochemical oxygen sensor includes, a sensor cap having one or more solid features defined on a top surface of the sensor cap. The electrochemical oxygen sensor further includes, a sensing electrode operable to sense oxygen, a counter electrode operable to generate oxygen, and an electrolyte. In accordance with said example embodiment, the electrochemical gas sensor also includes, a venting system including a vent conduit, a vent membrane, and an extended portion of the counter electrode. In this regard, the vent conduit of the venting system can be defined by an aperture in the sensor cap. The aperture can be dimensioned and configured such that it allows gas to vent out from the electrochemical oxygen sensor, however, prevents water from entering the electrochemical oxygen sensor at least partially through capillary forces. Further, the venting system described herein, can be operable to provide a passage to oxygen generated at the counter electrode, via the extended portion of the counter electrode to the vent membrane, and further via the vent conduit through the top surface of the sensor cap.

In accordance with said example embodiment, in an aspect, the sensor cap can be positioned at a top end of the electrochemical oxygen sensor. In this regard, the vent conduit of the venting system can be a channel defined from an open end at a top surface of the sensor cap, through the sensor cap, to one end at a bottom surface of the sensor cap and further to a portion of the vent membrane.

In accordance with said example embodiment, in another aspect, in the venting system, the vent membrane can be positioned over or adjacent to the counter electrode so that a portion of the vent membrane overlaps with the extended portion of the counter electrode, thereby defining a passage. In this regard, the passage defined can be such that the oxygen generated at the counter electrode may flow through the extended portion into the vent membrane, and further vent out through a top end of the electrochemical oxygen sensor, via an opening of the vent conduit.

In another aspect, in accordance with various example embodiments described herein, the extended portion of the counter electrode includes a first synthetic polymer having a first porosity defined within a first range. Further, the vent membrane includes a second synthetic polymer having a second porosity within a defined second range and a water ingress pressure within a defined range.

In another aspect, in some example embodiments, the venting system can be operable to provide a passage for gas inside the electrochemical oxygen sensor to be vented based on a pressure differential between inside and outside of the electrochemical oxygen sensor.

According to some example embodiments, a vent assembly for an EGS can include a vent membrane dimensioned and configured to have a defined porosity. Further, the vent assembly can include a vent conduit dimensioned and configured to release gas out from a portion of an EGS while preventing water to enter the EGS at least partially through capillary forces and an extended portion of a counter electrode. In this aspect, in accordance with some example embodiments, the venting assembly can be operable to provide a passage to a gas generated at the counter electrode of the EGS, via an extended portion of the counter electrode to the vent membrane, and further via the vent conduit through the portion of the EGS.

The above summary is provided merely for purposes of providing an overview of one or more exemplary embodiments described herein so as to provide a basic understanding of some aspects of the disclosure. Accordingly, it will be appreciated that the above-described embodiments are merely examples and should not be construed to narrow the scope or spirit of the disclosure in any way. It will be appreciated that the scope of the disclosure encompasses many potential embodiments in addition to those here summarized, some of which are further explained within the following detailed description and its accompanying drawings.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

Figure 1:
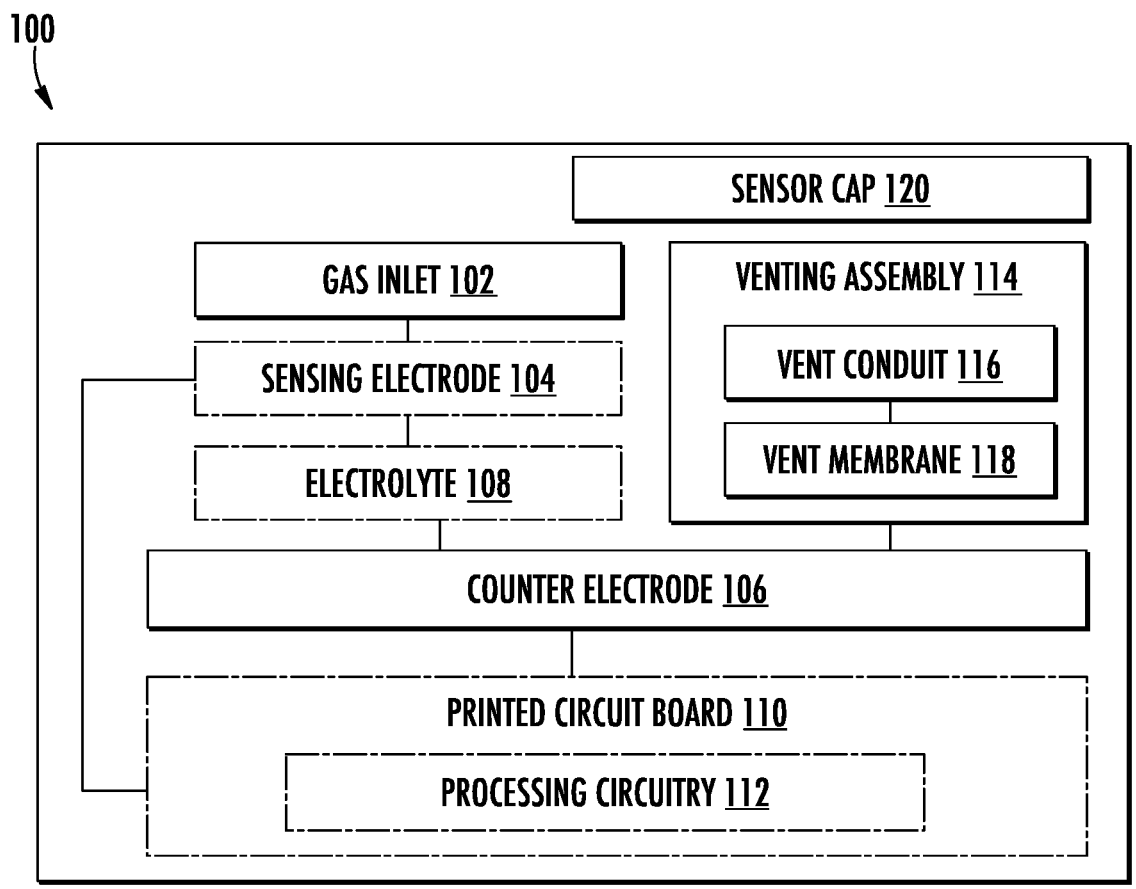
FIG. 1 schematically depicts a block diagram illustrating various components of an electrochemical gas sensor, in accordance with some example embodiments described herein.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout. Terminology used in this patent is not meant to be limiting insofar as devices described herein, or portions thereof, may be attached or utilized in other orientations.

The phrases "in one embodiment," "according to one embodiment," "in some embodiments," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

'Electrochemical gas sensors' (EGS) generally operate based on a 'redox' reaction that occurs inside the EGS, e.g., when a target gas is diffused inside an assembly of the EGS. Some EGS assemblies include two parts, for instance a first (upper) part and a second (lower) part, that are engaged together. However, while various embodiments described herein refer to upper and lower parts and top and bottom components, one of ordinary skill in the art will understand that a wide array of configurations of parts and components is included in the scope of this disclosure. Without wishing to be bound by any particular theory, during the redox reaction inside the EGS, a metal cathode in the first part of the EGS may chemically reduce oxygen from a target gas while a balancing reaction oxidizes an anode in the second part of the EGS. To this extent, in the EGS, the cathode and the anode can be coupled, operably coupled, fluidically coupled, and/or chemically coupled using an ionically conducting electrolyte. In this regard, a flow of current due to the redox reaction at the metal cathode and the anode provides a measurement of a concentration of the target gas detected by the EGS. The EGS assembly may also include a separator that may chemically, fluidically, and/or electronically separate or partially separate the first part of the EGS from second part of the EGS. In this aspect, the separator may partially define the bounds or extents of the first part and/or the second part of the EGS and may also become saturated with the electrolyte, e.g., in order to accommodate ion transfer therebetween. In some embodiments, the separator may also contact the metal cathode in the first part and support ion transfer between the metal cathode and the anode of the EGS.

Typically, during use, a gas, such as oxygen, diffuses into the first part of the sensor through an aperture such as, a capillary, a passage, a channel, or the like, and a gas phase diffusion barrier to react with the metal cathode. In this aspect, oxygen can be consumed by the sensor electrode of the EGS for measurement while oxygen can be generated by a counter electrode or the anode of the EGS as a balance to the redox reaction. The oxygen generated at the counter electrode, may cause degradation of the overall operational performance of the EGS. For instance, in some cases, the oxygen generated at the counter electrode enters the first part of the EGS including a sensing electrode, which results in an erroneous measurement of oxygen concentration by the sensing electrode. Also, at times, the generated oxygen descends towards the second part of the EGS, which may, optionally, include a printed circuit board (PCB) and associated electronic components. The flow of the oxygen generated at the counter electrode, in such cases, may cause an increase in humidity on a surface of the PCB and/or may result in condensation forming inside the electronic components, thereby degrading the overall EGS assembly, degrading the PCB and/or associated electronic components, causing a short circuit, causing a dilution of sensor electrode/counter electrode chemistry, or the like. Further, in another aspect, excessive accumulation of the generated oxygen inside the housing of the EGS creates a pressure differential inside the EGS as compared to pressure external to the EGS body, which may further cause a problem known as 'glitching'.

According to some embodiments, 'vents' may also be used for pressure relief in a fuel-cell type EGS, where drawbacks associated with parasitic consumption of the consumable component are not an issue, as in a case in which oxygen is generated at the counter electrode inside the EGS. Also, the EGS may work well initially, however, the operational performance may degrade over time. For example, in some instances, over time, the separator may start leaking inside the EGS, which may allow for bulk transfer of gas or other fluids between the first and second parts of the EGS. Further, in cases where the EGS is subjected to temperature changes, expansion or contraction of gas within the EGS may produce pressure gradients across the separator which can result in bubbles of gas being forced through the separator. When this occurs, gas may need to flow through the capillary of the sensor to compensate for the change in volume due to movement of the bubble(s), which is inconsistent with the principle of diffusion (i.e., inflow of gas inside the EGS through the capillary) under which the EGS operates. In such cases, the bulk transport of gas through the first part of the EGS causes the sensor to produce erroneous readings through a process commonly referred to as 'glitching'. Also, in some existing mechanisms, a vent defined by an aperture in a bottom portion of a sensor assembly of the EGS can be included, thereby abutting a corresponding device or instrument such that vented oxygen can be released into an inner volume of the corresponding device or instrument, which can cause instrument/device error and/or unsafe use conditions. Furthermore, some existing mechanisms include the use of a permeable membrane (e.g., PTFE tape) but a resulting condition arises wherein the gas (oxygen) can be not preferentially vented and instead permeates through the assembly and reaches the sensor electrode and/or when water permeates through the membrane. Thus, existing mechanisms for venting out the generated oxygen at counter electrode are inefficient and when implemented inside the EGS, complicates an overall design of the EGS.

In order to avoid glitching and to reduce the likelihood of undesirable exposure of the sensor electrode to gases such as oxygen generated at the counter electrode, embodiments disclosed herein may allow for increased and improved gas venting nearby the counter electrode, may allow for increased gas buildup in the EGS without an increase in inside pressure relative to outside pressure, and may also allow for increased durability of the EGS and components thereof.

Various example embodiments described herein, relate to an electrochemical gas sensor (EGS), and in particular to (i) an improved placement of a vent inside a sensor assembly of the EGS, (ii) an increased preferential venting of oxygen generated at the counter electrode inside the EGS, by using a membrane material having a higher porosity for a vent membrane, and (iii) an increased vent membrane durability through formation of support pillars on a portion of housing of the EGS about the vent membrane, in order to reduce deformation and damage of the vent membrane during assembly and use of the vent membrane in the EGS.

In some embodiments, the EGS can include a venting system. The venting system can be operable to provide a passage for gases generated at the counter electrode to be vented out from a body or a housing of the EGS. The venting system can include, according to some embodiments, a vent membrane having a defined porosity, a vent conduit, and an extended portion of the counter electrode. In this regard, the vent membrane can be located inside the EGS, e.g., at an end adjacent to or nearby a sensor cap of the EGS. Further, the vent conduit can be defined by an aperture through a top portion (e.g., through the sensor cap) of the EGS. The vent conduit can be operable to vent the gases, (for example, oxygen that may be generated during use of the EGS at the counter electrode), out from a top of the EGS. In this regard, inside the EGS, the vent conduit can extend from one end of the vent membrane through the sensor cap, and further to an open end of the sensor cap. For instance, in an embodiment in which the EGS can be configured to be coupled to a device such as an instrument, a printed circuit board (PCB), a surface, or the like, the sensor cap can be positioned such that the gas vents away from the instrument, the PCB, the surface, or the like. To this extent, upon assembling a first part and a second part of an assembly of the sensor, the vent membrane can be positioned over an extended portion of the counter electrode such that a portion of the vent membrane overlaps with the extended portion of the counter electrode, thereby defining the passage. Accordingly, the assembly of the EGS including the extended portion of the counter electrode, the vent membrane, and the vent conduit, at least partially defines the passage for oxygen generated at the counter electrode, such that at least a portion of the oxygen flows from the counter electrode to the vent membrane and further upwards, towards a top end of the EGS, through the vent conduit, and out of the body of the EGS through an open end of the sensor cap.

In accordance with some example embodiments, the extended portion of a counter electrode can include or be made of a synthetic polymer or a porous material, such as Polytetrafluoroethylene (PTFE) and/or other suitable materials that support passage of the oxygen generated at the counter electrode to the vent membrane of the venting system. Further, the vent membrane can also include or be made of a porous material having porosity relatively lower than a porosity of the portion of the counter electrode. In some embodiments, in order to promote sensor performance, each of the vent membrane and the extended portion of the counter electrode can be dimensioned and configured to have a thickness, a water ingress pressure, an airflow, a Gurley number, and/or a porosity within pre-defined ranges. Furthermore, the vent membrane of the venting system can be dimensioned and configured to have a defined surface area that facilitates sufficient accumulation of the oxygen before the oxygen can be eventually vented out of the EGS. The vent membrane, in accordance with some example embodiments, can be heat sealed with the top cap such that outflow of electrolyte from inside the EGS can be prevented, substantially prevented, or partially prevented, while at the same time allowing the oxygen or other generated gas to be vented from the EGS, e.g., via the vent conduit. In accordance with some example embodiments, the vent conduit can be dimensioned and configured such that any flow of water can be disallowed from entering the assembly of the EGS via the vent, e.g., due to capillary forces at least partially caused by the size and shape of the vent conduit.

In accordance with some example embodiments, on a portion of a top end of the EGS, for instance on the sensor cap, one or more solid features can be defined. In this regard, the one or more solid features may have any suitable form factor and can be formed by the addition or subtraction of any suitable material to or from the top end of the EGS. For instance, the solid features can be defined by an array of pillar-shaped moldings that protrude outwardly from a surface on the top end of the EGS. In this aspect, the one or more solid features can be positioned and dimensioned to prevent deformation of the vent membrane, prevent damage before, during, or after EGS assembly or use, and to retain a shape and/or a position of the vent membrane with regard to other components of the EGS. For instance, the solid features can be positioned and dimensioned to force the vent membrane to conform to a shape and/or a structure that prevents air-tight abutment of the vent membrane to the surface of the sensor cap, thereby avoiding any blocking of the vent conduit. Further, a cavity defined at least in part by the surface of the sensor cap, the interstitial spaces between the one or more solid features of the EGS, and the vent membrane may provide an increased volume inside the EGS. In some embodiments, the cavity provides a volume into which gases, such as at least a portion of the oxygen generated at the counter electrode, can disperse or be communicated, thereby avoiding or reducing a pressure inside the EGS. In other words, in some embodiments the lower porosity vent membrane of the venting system restricts venting of oxygen while the vent passage has sufficiently small dimensions so as to cause capillarity with respect to water, in which case the cavity provides a volume in which gas can be retained and/or through which gas can be communicated before venting. In some embodiments, as the gas accumulates during periods of increased oxygen generation and/or reduced gas venting capacity, the inner volume can be filled in order to maintain a desired pressure differential between the inside and the outside of the EGS.

In accordance with some example embodiments described herein, 'an electrochemical gas sensor' (EGS) as described herein, may correspond to an oxygen sensor that relies upon the principle of an oxygen pump. In some embodiments, for example when the EGS is an oxygen sensor, oxygen may be reduced at the sensing electrode and water may be oxidized at the counter electrode according to the following half reactions:

$$\text{At the sensing electrode: } O_2 + 4H^+ + 4e^- \rightarrow 2H_2O \quad \text{(Eq. 1)}$$

$$\text{At the counter electrode: } 2H_2O \rightarrow O_2 + 4H^+ + 4e^- \quad \text{(Eq. 2)}$$

In this aspect, an overall reaction inside the sensor may result in the consumption of oxygen, e.g., at the sensing electrode, with an approximately equivalent or equivalent production of oxygen, e.g., at the counter electrode. In other embodiments, other gases may be consumed and generated according to other half reactions to achieve a substantially balanced redox reaction similar to but different from that described herein with regard to the example oxygen sensor. In some embodiments, the overall reaction can optionally be maintained by means of a reference electrode and a potentiostat, the reference electrode and/or potentiostat being operable to lower a potential at the sensing electrode and allow the reaction to proceed. The resulting current between the sensing electrode and the counter electrode may be proportional to the oxygen concentration of the ambient gas and, accordingly, a concentration of target gas, e.g., such as oxygen, can be thereby measured and/or monitored by the oxygen sensor.

In the EGS, 'electrodes' generally allow for various reactions to take place to allow a current or potential to develop in response to a presence of a target gas such as, oxygen, in a concentration relative to other gases present. A resulting signal indicative of an occurrence of electrochemical reaction inside the EGS, may then be presented, communicated, or in other ways facilitate determination of the concentration of the target gas. The electrodes may comprise a reactive material suitable for carrying out a desired reaction. For example, the electrodes can be formed of a mixture of electrically conductive catalyst particles in a binder such as polytetrafluoroethylene (PTFE). In some embodiments in which the EGS is an oxygen sensor, the electrode may comprise carbon (e.g., graphite) and/or one or more metals such as copper, silver, gold, nickel, palladium, platinum, ruthenium, iridium, other suitable metals, oxides of these metals, or combinations thereof. The catalyst used can be a pure metal powder, a metal powder combined with carbon, a metal powder supported on an electrically conductive medium such as carbon, a combination of two or more metal powders either as a blend or as an alloy, or other suitable configurations. The materials used for the individual electrodes may be the same or different. The electrode can also comprise a backing material or substrate such as a membrane to support the catalyst mixture. The backing material or substrate can comprise a porous material to provide fluid (e.g., gas) access to the electrode through the substrate. The backing material may also be hydrophobic to prevent or substantially prevent the electrolyte from escaping from the housing. Also, the electrodes may be made by mixing the desired catalyst with a hydrophobic binder such as a PTFE emulsion and depositing the mixture on the backing material. The electrodes might be deposited onto the substrate, for example by screen printing, filtering in selected areas from a suspension placed onto the substrate, spray coating, any other method suitable for producing a patterned deposition of solid material, or combinations thereof. Deposition might be of a single material or of more than one material sequentially or otherwise in layers, so as to, for example, vary the properties of the electrode material through its thickness or to add a second layer of increased electrical conductivity above or below the layer which can be the main site of gas reaction.

The "separator" as described herein may comprise a nonwoven porous material (e.g., a porous felt member), a woven porous material, a porous polymer (e.g., an open cell foam, a solid porous plastic, etc.), or the like, and can be generally chemically inert with respect to the electrolyte and the materials forming the electrodes. In an embodiment, the separator may be formed from various materials that are substantially chemically inert to the electrolyte including, but not limited to, glass (e.g., a glass mat), polymer (plastic discs), ceramics, or the like.

The "electrolyte" as described herein, may comprise any aqueous electrolyte such as a solution of a salt, an acid, a base, or the like, depending on the target gas of interest. According to various example embodiments described herein, the electrolyte may comprise a hygroscopic acid such as sulfuric acid for use in an oxygen sensor. Other target gases may use the same or different electrolyte compositions. In addition to aqueous based electrolytes, ion liquid electrolytes may also be used to detect certain gases.

In accordance with various embodiments a 'vent membrane' as described herein, may comprise, include, be partially formed from, or be formed from any of polytetrafluoroethylene (PTFE), fluorinated ethylene propylene (FEP), polyethylene (PE), polypropylene (PP), polymethyl methacrylate (PMMA), polyethylene terephthalate (PET) polyaryletheretherketone (PEEK), perfluoro alkoxy (PFA), ethylene chlorotrifluoroethylene (E-CTFE), any other suitably porous and durable materials, and/or any combination thereof. In some embodiments, the vent membrane can be formed by removal of material from a bulk material, by addition of material to a substrate, by weaving or otherwise interlocking discrete portions of one or more materials (e.g., by weaving), by extruding one or more materials, by foaming one or more materials, or by any other suitable method.

In accordance with various embodiments, a "body molding" of an electrochemical gas sensor as described herein, may comprise, be partially formed from, or be formed from materials that are inert with regard to a selected electrolyte. For example, in accordance with some example embodiments, the body moldings, a sensor cap, and/or a base may comprise, be partially formed from, or be formed from one or more plastic or polymeric materials. In this aspect, the body molding, the sensor cap, and/or the base may comprise, be partially formed from, or be formed from a material including, but not limited to, acrylonitrile butadiene styrene (ABS), polyphenylene oxide (PPO), polystyrene (PS), polypropylene (PP), polyethylene (PE) (e.g., high density polyethylene (HDPE)), polyphenylene ether (PPE), or any combination or blend thereof.

FIG. 1 schematically depicts a block diagram illustrating various components of an electrochemical gas sensor (EGS) 100, in accordance with some example embodiments described herein. In some embodiments, the EGS 100 includes a gas inlet 102. The gas inlet 102 may be in fluidic communication with an electrode of an electrochemical cell of the EGS 100 and may be operable to facilitate an inflow of a target gas inside the EGS 100. In some embodiments, the gas inlet 102 may be defined by an aperture, an orifice, a passageway, a channel, a capillary, or the like. The gas inlet 102 may extend through a portion of a housing of the EGS 100 such that, during operation of the EGS 100, the target gas may be communicated into, caused to diffuse into, or otherwise be disposed within the EGS 100 for purposes of gas concentration measurement and/or monitoring. In some embodiments, the EGS 100 further includes a sensing electrode 104, a counter electrode 106, and an electrolyte 108. In some embodiments, the sensing electrode 104, the counter electrode 106, and the electrolyte 108 comprise an electrochemical cell (not shown). In some embodiments, the electrochemical cell can be configured such that the sensing electrode 104 and the counter electrode 106, with the electrolyte 108, form a circuit whereby ions can be communicated between the sensor electrode 104 and the counter electrode 106 via the electrolyte 108 and electrons are communicated in an opposite direction between the counter electrode 106 and the sensor electrode 104, creating a measurable current flow. In some embodiments, the sensing electrode 104 may be operably coupled, ionically coupled, electrically coupled, and/or fluidically coupled to the counter electrode 106, e.g., via the electrolyte 108. The EGS 100 may optionally include a reference electrode (not shown). In accordance with various example embodiments described herein, the sensing electrode 104 may also be referred as a 'working electrode', a 'first electrode', or a 'consuming electrode' and typically refers to the electrode that is configured to be exposed to and to consume at least a portion of the target gas during measurement of the concentration of the target gas. According to various example embodiments, the EGS 100 or components thereof, may be operable to monitor a concentration of the target gas, for example oxygen, based on a redox reaction which takes places when the target gas is diffused inside the EGS 100. To this extent, the electrochemical cell including the sensing electrode 104 may consume the target gas and transmit ions through the electrolyte 108 to the counter electrode 106, and the counter electrode 106 can generate the target gas such that measurement of the concentration of the target gas is achieved by measuring a flow of current or a potential difference between the sensor electrode 104 and the counter electrode 106 that may be generated due to the electrochemical reaction inside the electrochemical cell.

In some embodiments, the EGS 100 can optionally include a printed circuit board (PCB) 110 comprising a processing circuitry 112 that may be configured to receive a digitized output indicative of values corresponding to the electric current or the voltage generated inside the electrochemical cell of the EGS 100. In this aspect, in accordance with various example embodiments described herein, the processing circuitry 112 may process such values to determine a concentration of the target gas. In another example embodiment, the PCB 110 and the processing circuitry 112 may be located external to the EGS 100. In this regard, in some examples, one or more electrical contacts of the EGS 100 may connect with the externally located PCB 110 and the associated processing circuitry 112. In some embodiments, the PCB 110 and the processing circuitry 112 may be located in a remote device which may be connected with the EGS 100, for instance, over a wired or wireless communication network or based on some electrical connection. In such cases, the PCB 110 and the processing circuitry 112 may access signal values from the EGS 100 and perform the processing remotely.

According to various example embodiments described herein, the EGS 100 includes a venting assembly 114 that is operable to provide a passage to various gases that are generated inside the EGS 100, and are to be vented out from a body of the EGS 100. In some embodiments, these gases may be generated due to the electrochemical reaction which takes place inside the electrochemical cell, i.e., at the counter electrode 106, the sensing electrode 104, or elsewhere in the electrochemical cell, upon exposure to the target gas. For example, in some example embodiments, the redox reaction at the sensing electrode 104 and the counter electrode 106 due to diffusion of the target gas inside the EGS 100 may generate oxygen at the counter electrode 106. It may be desired to vent at least some of this generated oxygen out of the EGS 100. In accordance with some example embodiments, the venting assembly 114 can include a vent conduit 116, a vent membrane 118, and/or an extended portion of the counter electrode 106. In some embodiments, the vent conduit 116, the vent membrane 118, and the extended portion of the counter electrode 106 can be substantially aligned and/or positioned nearby one another such that at least a portion of the gas generated at the counter electrode 106 can be communicated from the extended portion of the counter electrode 106, through the vent membrane 118, and through the vent conduit 116 to ambient. In this aspect, the vent membrane 118 of the venting assembly 114 may be in fluidic communication with the counter electrode 106 of the EGS 100. In some embodiments, the vent membrane 118 may be dimensioned and configured to have a defined porosity that supports ingress and egress of gases through its membrane. Furthermore, in accordance with some example embodiments, at least one of the vent conduit 116 and the vent membrane 118 may be dimensioned and configured such that the gas generated inside the EGS 100 may vent from the EGS 100 to the outside via the vent conduit 116, however, any water present in environment outside the EGS 100 may be prevented from entering the EGS 100 at least partially through any capillary forces generated inside the vent conduit 116 of the EGS 100.

In accordance with some example embodiments, the EGS 100 can comprise a sensor cap 120 including one or more solid features (not shown) that defines a cavity inside the EGS 100. The cavity described herein may be defined based on interstitial spaces between one or more solid features on a surface of the sensor cap 120 and the vent membrane 118 of the venting assembly 114. In some embodiments, the one or more solid features may have any suitable form factor and can be formed by the addition or subtraction of any suitable material to or from the top end of the EGS 100. For instance, the solid features can be defined by an array of pillar-shaped moldings that protrude outwardly from a surface on the top end (e.g., a surface of the sensor cap 120) of the EGS 100. In this aspect, the one or more solid features can be positioned and dimensioned to prevent deformation of the vent membrane 118, prevent damage to the vent membrane 118 before, during, or after EGS 100 assembly or use, and to retain a shape and/or a position of the vent membrane 118 with regard to other components of the EGS 100. For instance, the solid features can be positioned and dimensioned to force the vent membrane 118 to conform to a shape and/or a structure that prevents air-tight abutment of the vent membrane 118 to the surface of the sensor cap 120, thereby avoiding any blocking of the vent conduit 116. Further, a cavity defined at least in part by the surface of the sensor cap 120, the interstitial spaces between the one or more solid features of the EGS 100, and the vent membrane 118 may provide an increased volume inside the EGS 100. In some embodiments, the cavity provides a volume into which gases, such as at least a portion of the oxygen generated at the counter electrode 106, can disperse or be communicated, thereby avoiding or reducing a pressure inside the EGS 100. In other words, in some embodiments the lower porosity vent membrane 118 of the venting assembly 114 may restrict venting of oxygen while the vent conduit 116 has sufficiently small dimensions so as to cause capillarity with respect to water, in which case the cavity provides a volume in which gas can be retained and/or through which gas can be communicated before venting. In some embodiments, as the gas accumulates during periods of increased oxygen generation and/or reduced gas venting capacity, the inner volume can be filled in order to maintain a desired pressure differential between the inside and the outside of the EGS 100. Further details related to various components and associated operations of the EGS 100 are described in FIGS. 2-7 hereinafter. Various aspects of the embodiments of FIGS. 2-7 are substantially similar to the embodiments described above with respect to FIG. 1. Therefore, substantially similar aspects are not described in complete detail below. For instance, in some embodiments, a sensing electrode 222 from FIG. 2 may be substantially similar to the sensing electrode 104 and may not be described in further detail below.

Figure 2:
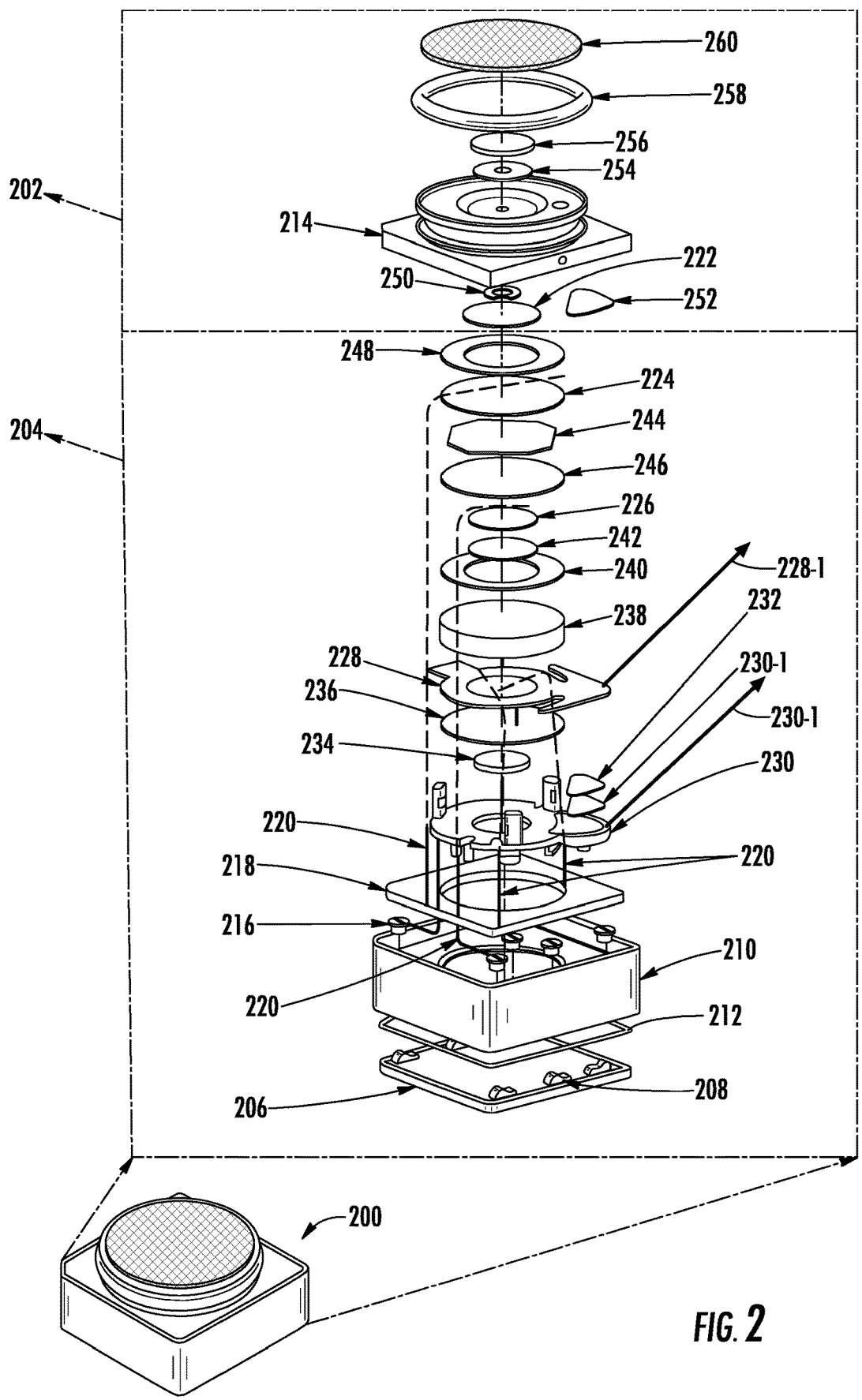
FIG. 2 schematically depicts an exploded view of an electrochemical gas sensor, in accordance with some example embodiments described herein.

FIG. 2 schematically depicts an exploded view of an electrochemical gas sensor (EGS) 200, in accordance with some example embodiments described herein. In some embodiments, the EGS 200 includes a first part 202 and a second part 204 that may be adapted to be engaged over each other or coupled together to form a housing of the EGS 200, e.g., while assembling various components of the EGS 200, described hereinafter. Starting at a lower end, in some embodiments, the second part 204 of the EGS 200 can include a printer circuit board (PCB) 206. In some embodiments, the EGS 200 may not include the PCB 206, but rather the EGS 200 can be operably coupled to an external PCB or other such device such that measurements and/or signals indicative of measurements made by the EGS 200 can be transmitted, stored, and/or presented. The PCB 206, in accordance with various example embodiments described herein, can be adapted to connect the EGS 200 to external circuitry (not shown). In some embodiments, the EGS 200 can include internal sensor pads (not shown) configured to be coupled to one or more sensor pads (not shown) of the external circuitry in order to couple the EGS 200 and the external circuitry, which may be external to the EGS 200, as shown in FIG. 2, or can be incorporated into the EGS 200 at least in part. In some embodiments, the PCB 206 may be configured to provide a digitized output of the EGS 200, e.g., to a processor, computing device, user display, or any other suitable instrument or device. In this regard, the digitized output may be related to a target gas monitored by the EGS 200. In some embodiments, the digitized output can include a signal or other transmission form indicative of a concentration of the target gas being monitored. In some embodiments, the digitized output can include a signal or a plurality of signals or other transmission forms indicative of a change in the concentration of the target gas being monitored over time. In some embodiments, the digitized output is a burst or intermittent stream of batch-wise target gas concentration values over time or a steady stream of real-time or near real-time target gas concentration values. In some embodiments, the signal or other transmission form can include or be a signal or other transmission form indicative of a current or potential between or within an electrochemical cell of the EGS 200. In this regard, the current may flow, e.g., between one or more electrodes (not shown), due to a redox reaction which occurs at the one or more electrodes of the EGS 200, in response to exposure to the target gas inside the EGS 200. In some embodiments, the PCB 206 may include circuitry for measuring the current and controlling bias on the EGS 200. In some embodiments, the PCB 206 may include one or more connector elements 208. Additionally, or alternatively, the PCB 206 may include a processing circuitry that is configured to enable diagnostics to be executed on the EGS 200.

In accordance with some example embodiments, the PCB 206 may be coupled to, disposed upon, or otherwise affixed to a body molding 210 of the EGS 200, e.g., via a PCB adhesive 212, through the one or more connector elements 208. In this aspect, the body molding 210 of the EGS 200 can be adapted to contain various electrochemical components and/or other components of the EGS 200. In this regard, in some example embodiments, the body molding 210 can be designed to be engaged mechanically with a sensor cap 214 of the EGS 200. In this aspect, in some example embodiments, the body molding 210 may be hermetically sealed or substantially hermetically sealed to the sensor cap 214 and other PTFE membranes inside of the EGS 100. The body molding 210 may also include a filler hole (not shown) for facilitating addition of the electrolyte to the EGS 200 after the EGS 200 has been partially or fully assembled. According to some example embodiments, the body molding 210 is also designed to retain one or more contact pads 216 of the EGS 200. The one or more contact pads 216 may be adapted to conduct current generated by the electrochemical cell of the EGS 200 to an interface of the PCB 206. In this regard, upon assembling at least some of the various illustrated components of the EGS 200, the one or more contact pads 216 may be retained in the body molding 210 of the EGS 200. To this extent, in accordance with some example embodiments, the one or more contact pads 216 may be adapted to be corrosion resistant and tolerant to one or more materials which may be present or generated inside the EGS 200, for instance, sulfuric acid. Alternatively, in some example embodiments, where the one or more contact pads 216 are not adapted to be corrosion resistant, an epoxy 218 can be used to protect the one or more contact pads 216 from corroding. In some example embodiments, the one or more contact pads 216 can be adapted to conduct current generated by the electrochemical cell of the EGS 200 without regard to corrosion resistance. For example, in some embodiments, the one or more contact pads 216 can be replaceable, can include sacrificial material such that corrosion is an aspect of designed function during use, and/or can be formed from or partially formed from a material that helps limit or eliminates corrosion of the one or more contact pads 216 during use of the EGS 200.

In some embodiments, the epoxy 218 may be adapted to provide a sealing between the one or more contact pads 216 and the body molding 210, thereby preventing any leakage outside from the EGS 200 when the components of the EGS 200 are assembled together. In this aspect, in accordance with some example embodiments described herein, a material or one or more of the materials of the epoxy 218 may be selected such that, the epoxy 218 is adapted to maintain seal integrity, even in extreme operating conditions, during use of the EGS 200. For instance, in accordance with some example embodiments, the epoxy 218 may be adapted to maintain seal integrity when the EGS 200 is operated under temperature conditions within a range from about −50° C. to about 70° C., about −40° C. to about 60° C., about −40° C. to about 70° C., about −30° C. to about 60° C., about −50° C. to about 40° C., or about −20° C. to about 70° C., inclusive of all values and ranges therebetween. In some embodiments, the epoxy 218 may be adapted to maintain seal integrity when the EGS 200 is operated under temperature conditions greater than about 20° C., about 30° C., about 40° C., about 50° C., about 60° C., or about 70° C., inclusive of all values and ranges therebetween. In some embodiments, the epoxy 218 may be adapted to maintain seal integrity when the EGS 200 is operated under temperature conditions less than about 0° C., −10° C., −20° C., −30° C., −40° C., or −50° C., inclusive of all values and ranges therebetween. In this aspect, the epoxy 218 may at least partially seal the one or more contact pads 216 in order to prevent contact with an internal electrolyte in the EGS 200.

In some embodiments, one or more current collecting wires 220 can be connected to the one or more contact pads 216, respectively. The multiple current collecting wires 220 can be adapted to provide an electrical connection between one or more electrodes of the EGS 200, and further to one or more external contact pads on the PCB 206. For instance, in some embodiments, the one or more current collecting wires 220 may form one or more electrical connections with various components, including but not limited to a sensing electrode 222 via a separator 224, a reference electrode 226, and a counter electrode 228. In some example embodiments, the multiple current collecting wires 220 may be coupled to the one or more contact pads 216 and, optionally, may be sealed within the epoxy 218. Further, the EGS 200 can include a support table 230 that may be configured to provide support for stacking various sensor components of the EGS 200. In some embodiments, the support table 230 may provide support for ensuring a compression pressure among or a spacing distance between the various sensor components is sufficient once the components of the EGS 200 are stacked and the EGS 200 is fully assembled. In accordance with some example embodiments, the support table 230 can include one or more venting slots 230-1 for locating and positioning one or more venting components, such as vent separators 232, that may facilitate venting of gases present inside the EGS 200. In some embodiments, the support table 230 can be dimensioned and configured so as to avoid at least some of the distortion that sometimes occurs due to stacking of various components of gas sensors such as the EGS 200. In accordance with some example embodiments, the support table 230 may also provide an area for heat sealing the counter electrode 228 of the EGS 200.

In some embodiments, the EGS 200 can include a carbon cloth 234 that may be adapted to fit into a recess on the support table 230 as the components of the EGS 200 are stacked together. In some embodiments, the EGS 200 can further include a central vent membrane 236 that may be heat sealed inside the support table 230 and adapted to retain an electrolyte. In some embodiments, the central vent membrane 236 may allow gas to pass therethrough, for instance when gas is generated as part of a counter reaction inside the EGS 200. To this end, the central vent membrane 236, in some example embodiments, may be dimensioned and configured to allow various sensor components to exchange gases with the ambient environment outside the EGS 200 through one or more capillaries, apertures, orifices, or other such passageways of the central vent membrane 236, such that gas generated as a part of the counter reaction can be diffused in all orientations, embodiments, and configurations of the EGS 200. Additionally, and/or alternatively, the central vent membrane 236 may allow any oxygen generated as part of an oxidation counter reaction to vent from the EGS 200. In some embodiments, the central vent membrane 236 may allow gas to diffuse into the sensor body of the EGS 200 from the outside atmosphere, thereby equalizing pressure between the exterior and interior of the EGS 200. In this aspect, the central vent membrane 236 may be provided such that an adequate stack compression can be achieved to maintain an electrolyte free interface between the central vent membrane 236 and the counter electrode 228 of the EGS 200. In some embodiments, the central vent membrane 236 may be designed such that the membrane does not split or otherwise crack during heat sealing and/or during assembly of various components of the EGS 200.

In some embodiments, the counter electrode 228 can be positioned between the central vent membrane 236 and a wick 238. The counter electrode 228, in accordance with various example embodiments described herein, can include an extended portion 228-1 that may include or be made from a synthetic polymer or a porous material, e.g., polytetrafluoroethylene (PTFE), which supports the communication of the gases through various pores on the extended portion 228-1. In some embodiments, the extended portion 228-1 of the counter electrode 228 may be dimensioned and configured to have a defined porosity within a defined porosity range that allows the communication of gases that may be generated at the counter electrode 228 through the extended portion 228-1. Details related to the porosity of the extended portion 228-1 of the counter electrode 228 and associated ranges are described further below in reference to FIG. 7. The counter electrode 228 may also include one or more breather tabs (not shown) depending on a circumference of an electrode tape of the counter electrode 228. In this regard, the one or more breather tabs may be dimensioned and configured to provide a path for the gases generated inside the EGS 200 to flow out of the EGS 200. As the counter electrode 228 is described in more detail below in reference to FIG. 7, further detail is not provided here.

In accordance with some example embodiments described herein, the sensing electrode 222 may correspond to an electrode at which at least a portion of a 'redox reaction' takes place upon diffusion of the target gas into the EGS 200. The redox reaction described herein, according to some embodiments, may correspond to an electrochemical reaction involving a reduction reaction at the sensing electrode 222 and a balancing oxidation reaction at the counter electrode 228. The counter electrode 228, in some embodiments, may correspond to an electrode at which current flows upon the reaction at the sensing electrode 222. In this regard, in accordance with various example embodiments, to balance a reaction at the sensing electrode 222 a counter reaction takes place at the counter electrode 228 and vice versa. For example, in an example situation, if oxidation occurs at the sensing electrode 222 (also referred as working electrode), a reduction reaction takes place the counter electrode 228 (also referred as auxiliary electrode). The reference electrode 226, in some examples, may correspond to an electrode having a stable electrode potential. In this aspect, the reference electrode 226 may provide a measure of potential at working electrode without passing current through the reference electrode 226. Further, the reference electrode 226 may be configured to provide a stable reference potential desired for an electrochemical oxygen pump reaction that may occur inside the EGS 200 during operation of the EGS 200.

In some embodiments, the wick 238 can be adapted to wick an electrolyte, as desired, through a stack of the various components of the EGS 200. In this aspect, the wick 238 may capture the electrolyte from a body cavity of the EGS 200 to maintain a liquid level throughout at least a portion of the stack of components of the EGS 200. Further, the wick 238 may provide an ionic pathway for electrochemical pump action to occur inside the EGS 200. The wick 238 may also provide a wetted interface for the counter electrode 228 and prevent or partially prevent the target gas, for example oxygen, generated at the counter electrode 228 from reaching the sensing electrode 222.

In some embodiments, the EGS 200 can further include a ring separator 240 and a gas barrier 242. The gas barrier 242, in accordance with some example embodiments, may be dimensioned and configured to act as a barrier for the gases below the gas barrier 242 such that the gases below the gas barrier 242 are prevented from reaching the sensing electrode 222. In some example embodiments, the gas barrier 242 may help reduce or minimize the amount of oxygen generated at the counter electrode 228 that reaches the reference electrode 226, positioned above the counter electrode 228 in the stack of the EGS 200. In accordance with some example embodiments, upon assembling the various components of the EGS 200, the gas barrier 242 can cover a bottom side of the reference electrode 226. In some embodiments, the EGS 200 can further include a separator 246, a gas barrier 244, and a ring separator 248 between the sensing electrode 222 and the reference electrode 226. In this aspect, the gas barrier 244 is adapted to provide similar functionality as the gas barrier 242. For instance, the gas barrier 244 may be dimensioned and configured to reduce or minimize the amount of oxygen generated at the counter electrode 228 that reaches the sensing electrode 222. In some embodiments, the gas barrier 244 may also provide an ionic contact between the separators, for instance between the separator 246 and the ring separator 248. In accordance with some example embodiments, the gas barrier 244 may also provide support for stable operation of the reference electrode 226 by preventing oxygen around the reference electrode from being consumed by the sensing electrode 222. Additionally, and/or alternatively, in some example embodiments, at least one of the gas barrier 242, the gas barrier 244, the separator 246, and the ring separator 248 may act as a barrier such as a barrier against any gases or oxygen diffusing up from the reference electrode 226 to the sensing electrode 222.

In accordance with some example embodiments, the separator 246 and the ring separator 248 may be dimensioned and configured to provide a crossover path to the sensing electrode 222 and the reference electrode 226 inside the EGS 200. In this aspect, the separator 246 and the ring separator 248 may also provide an ionic pathway for an electrochemical pump action to occur inside the EGS 200.

In some embodiments, the EGS 200 can include the sensing electrode 222 positioned between a diffuser disc 250 and the ring separator 248. In accordance with various example embodiments described herein, the sensing electrode 222 can be dimensioned and configured to provide a medium for electrochemical reaction of the target gas that may be diffused inside the EGS 200 through an aperture, an orifice, a capillary, or other such passageways through the sensor cap 214. In this aspect, in some example embodiments, the sensing electrode 222 may comprise or be made from a material that provides sufficient activity for reducing oxygen that may contact a surface of an electro catalyst present on the sensing electrode 222. In this regard, a structure of the sensing electrode 222 may also be dimensioned and configured to facilitate lateral gas diffusion to the electro catalyst perpendicular to an axis of the capillary. The sensing electrode 222 may also be dimensioned to be suitably coupled, e.g., heat sealed, with a body or housing of the sensor cap 214.

In accordance with various example embodiments described herein, the vent membrane 252 may be configured to be coupled with (e.g., heat sealed to) a portion of the sensor cap 214. In some embodiments, the vent membrane 252 may also be dimensioned and configured to provide a liquid barrier and protect the vent capillary from communication of an electrolyte therethrough. In accordance with some example embodiments, upon assembling the components of the EGS 200, the vent membrane 252 may be part of a venting system and may be positioned over, adjacent to, nearby, suitably proximal to, or otherwise within a suitable distance from the extended portion 228-1 of the counter electrode 228 such that the vent membrane 252 allows the gases generated at the counter electrode to be vented from the EGS 200 through a vent conduit defined by the sensor cap 214. In this aspect, the vent membrane 252 may be designed to have an operating temperature within a predefined operating temperature range and may have a defined operational life. Further, the vent membrane 252 may comprise or be made of a material such as, a synthetic polymer with a defined porosity that allows gases inside the EGS 200 to be diffused within the body of the EGS 200 in any direction and at all orientations of the EGS 200 so as to provide a pressure relief inside the EGS 200. To this extent, in some embodiments, the vent membrane 252 may be configured to also allow the gases inside the EGS 200 to diffuse into the body of the EGS 200 such that the pressure between the outside and the inside of the EGS 200 is similar, substantially equal, or equal. Also, in accordance with some example embodiments, the vent membrane 252 may be designed so as to not split or otherwise deform during heat sealing and assembly of the EGS 200. Further details of the vent membrane 252 and operations related to the venting of the gases inside the EGS 200 through the vent membrane 252 are described in FIGS. 3-7.

In accordance with some example embodiments, the diffuser disc 250 may be configured to diffuse gases across back of the sensing electrode 222. In this aspect, the diffuser disc 250 may be fitted within a defined area of the sensor cap 214, e.g., when various components of the EGS 200 are assembled. In this aspect, the diffuser disc 250 may be dimensioned and configured so as to avoid the collapse of the diffuser disc 250 due to stack compression of the EGS 200, e.g., during assembly. Further, the diffuser disc 250 may also be dimensioned and configured so as to occupy a minimal volume within the EGS 200 in order to minimize dead space above the sensor electrode 222.

In some embodiments, the first part 202 of the EGS 200 can also include an adhesive ring 254, a bulk flow and condensation assay 256, an O-ring 258, and a mesh outer cover 260 that may be assembled above the sensor cap 214. In some embodiments, the sensor cap 214 can be configured such that, during assembly of the EGS 200, the sensor cap 214 can be mechanically coupled to or engaged about the body molding 210 of the EGS 200, e.g., via the epoxy 218.

In accordance with various example embodiments described herein, the sensor cap 214 of the EGS 200 can include a vent conduit (not shown herein) to provide for venting of the gases from inside the EGS 200 to outside of the EGS 200. Details related to the vent conduit of the sensor cap 214 are described in reference to FIGS. 3-7. The sensor cap 214 may define a capillary (similar to the gas inlet 102) that may be adapted to facilitate an inflow of the target gas into the EGS 200. In accordance with various example embodiments described herein, the sensor cap 214 may be dimensioned and configured to allow for heat sealing of the sensing electrode 222 and the vent membrane 252. The sensor cap 214 may also include features or define areas that allow for secure positioning of the O-ring 258 and the diffuser disc 250 while assembling the EGS 200. The sensor cap 214, in some example embodiments, may allow a predefined rate of the target gas into the EGS 200 via the capillary and may also allow for venting of a predefined rate of excess gases generated inside the EGS 200 via the vent conduit. To this extent, according to some example embodiments, a capillary defined by the vent conduit of the sensor cap 214 that is adapted to facilitate the egress of the gases may be defined by a larger aperture than the capillary of the sensor cap 214 that is adapted to facilitate ingress of the target gas into the EGS 200. The sensor cap 214 may also include features or define areas that are dimensioned to accept the mesh outer cover 260 and the bulk flow and condensation assay 256. Further details related to the placement of the sensor cap 214 with respect to the body molding 210 of the EGS 200 are described in FIGS. 3-7.

In accordance with various example embodiments, the bulk flow and condensation assay 256 can be adapted to make contact with an area around the capillary on the sensor cap 214 and provide a suitable entry path for ingress of the target gas to the EGS 200. In this aspect, the bulk flow and condensation assay 256 can be adapted to restrict a sudden flow of the target gas into the EGS 200 and to avoid any compromise to diffusion control inside the capillary of the sensor cap 214. In some embodiments, the bulk flow and condensation assay 256 can also be adapted to facilitate a continued supply of the target gas into the capillary during condensing conditions. For example, according to some embodiments, condensing conditions may correspond to any condition where a relative humidity (RH) of the ambient air exceeds 100%, or where a temperature of the EGS 200 is lower than the dew point of the ambient air. For instance, condensing conditions may occur when a cold EGS 200 is put into a hot humid environment. For example, if the EGS 200 is stored or operated at a temperature of −20° C. for a sufficient period of time and is then transferred to an ambient temperature of +20° C., and if RH at +20° C. is greater than 4.5%, that is equivalent to greater than 100% RH at −20° C. and condensation will occur. Accordingly, in such cases, the bulk flow and condensation assay 256 may facilitate a continued supply of the target gas into the capillary.

In some embodiments, the adhesive ring 254 may be adapted to create a seal between the bulk flow and condensation assay 256 and the sensor cap 214 so as to control peak pressure transients. In this regard, the adhesive ring 254 can be dimensioned and configured to fit onto a feature or depression or other such area defined on or in a surface of the sensor cap 214. In accordance with some example embodiments, the adhesive ring 254 may also be adapted to prevent any water ingress between the bulk flow and condensation assay 256 and the sensor cap 214 once the EGS 200 is fully assembled.

In some embodiments, the EGS 200, at a top end, can include the mesh outer cover 260 supported by the O-ring 258. The O-ring 258, in accordance with some example embodiments, may provide compressive force against the body of the EGS 200 once assembled, and may further maintain seal integrity in various normal and harsh operating condition of the EGS 200. In some embodiments, the mesh outer cover 260 can be dimensioned and adapted to cover a top of the EGS 200 and allow air to flow into the bulk flow and condensation assay 256. The mesh outer cover 260 may also protect the capillary of the sensor cap 214 from dust ingress during storage and transportation of the EGS 200. Having described the exploded view including various components of the EGS 200 in FIG. 2, various aspects related to the EGS 200, in particular, related to a venting system of the EGS 200 and geometry of a top end of the EGS 200 including one or more solid features, are described in FIGS. 3-7 respectively.

Figure 3:
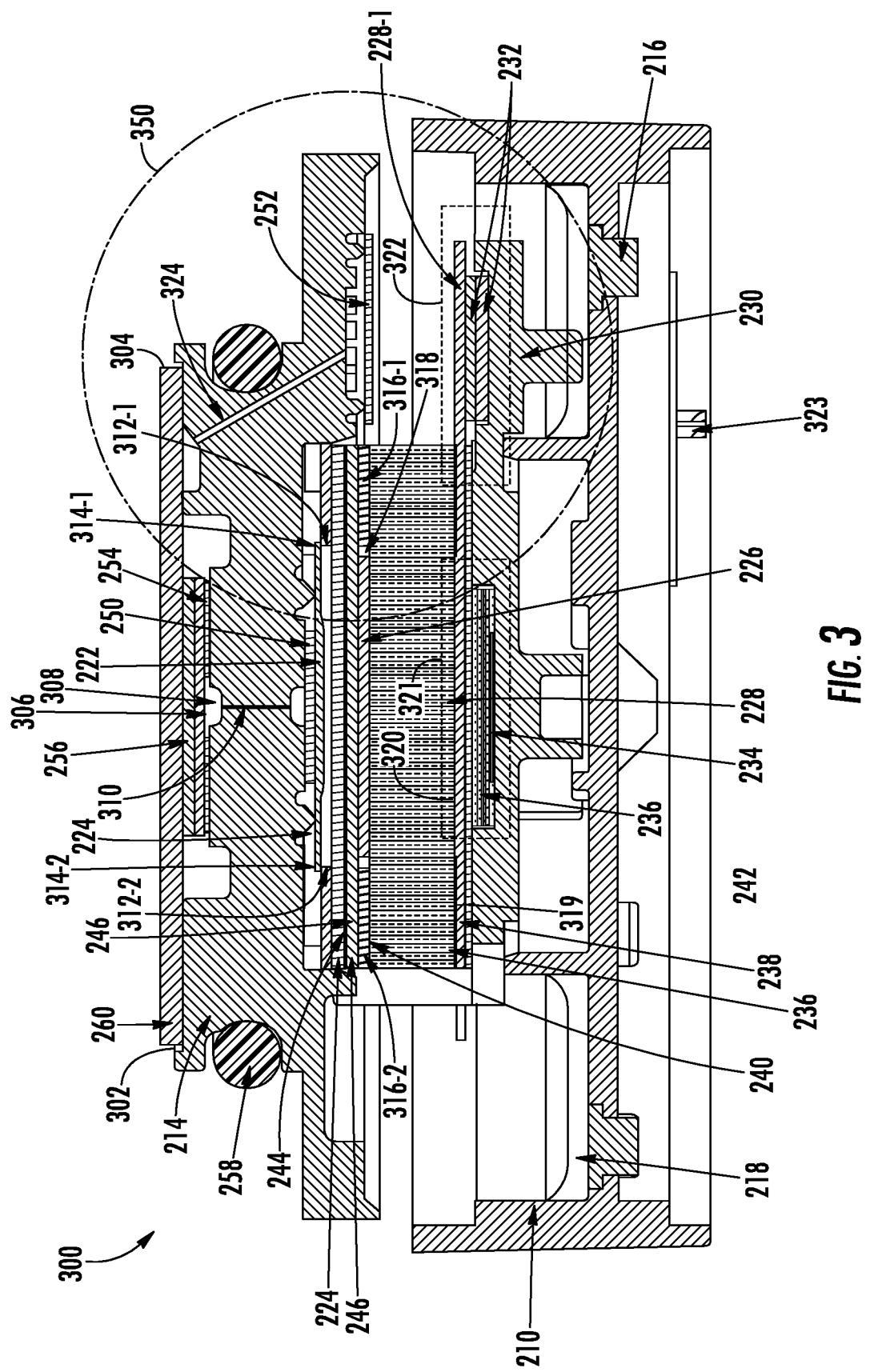
FIG. 3 schematically depicts a sectional view of the electrochemical gas sensor representing an internal structure of the electrochemical gas sensor, in accordance with some example embodiments described herein.

FIG. 3 schematically depicts a sectional view of the EGS 200 representing an internal structure of the EGS 200, in accordance with some example embodiments described herein. Starting at a top end, in some embodiments, the EGS 200 includes the mesh top cover 260 that can be positioned over the sensor cap 214. In this aspect, as illustrated, the mesh top cover 260 may be seated in a recess of the sensor cap 214. The recess may be defined at a top surface of the sensor cap 214 and may be of a shape complimentary to the mesh cover top 260. The recess herein can include an aperture with two protruded ends, i.e. about a first end 302 and a second end 304 of the sensor cap 214 that abuts with the mesh top cover 260 upon engagement of the mesh top cover 260 over the sensor cap 214. As illustrated from the sectional view, the O-ring 258 can be engaged around a cross-section of the sensor cap 214, thereby providing a sealing to the assembly of the EGS 200 and preventing any leakage during an operation of the EGS 200.

Illustratively, the sectional view representing an assembly of the EGS 200 can include the bulk flow and condensation assay 256 and further the adhesive ring 254 positioned coaxially to each other between a bottom surface of the mesh top cover 260 and a surface of the sensor cap 214. In some embodiments, the adhesive ring 254 defines an aperture 306 which further extends and mates to an opening 308 on the sensor cap 214. To this extent, the opening 308 of the sensor cap 214 extends further to define a capillary 310. The capillary 310 can be defined as a channel that through passes into a substrate of the sensor cap 214 from the opening 308 and up to another opening 312 of the sensor cap 214 that opens to the diffuser disc 250. In accordance with various example embodiments described herein, the capillary 310 can act as a gas inlet such that, air mixture including a target gas can inflow into the EGS 200 from the opening 308 and via the capillary 310. Illustratively, a bottom portion of the diffuser disc 250 mates with a top surface of the sensing electrode 222. As illustrated in FIG. 2, the ring separator 248 can include an aperture that can be dimensioned to receive the sensing electrode 222. To this end, the sectional view illustrates the ring separator 248 having two ends of its aperture 312-1 and 312-2 that abuts about two ends 314-1 and 314-2 on the periphery of the sensing electrode 222 respectively. Further, the ring separator 248 also abuts with the separator 224. Illustratively, the gas barrier 244 can be positioned between the separator 224 and the separator 246. In some example embodiments, the separators viz. the separator 224 and the separator 246, are operable to isolate the sensing electrode 222 with components below the separator 246 in the EGS 200 assembly, thereby preventing chances of the sensing electrode 222 for being exposed to gases that may raise up during an operation of the EGS 200. Illustratively, a bottom surface of the separator 246 abuts the ring separator 240 from two ends 316-1 and 316-2 respectively. To this extent, the ring separator 240 can include an aperture that can include the two ends 316-1 and 316-2 defined along a periphery of the aperture and can be dimensioned to receive the reference electrode 226 and the gas barrier 242 respectively between the two ends 316-1 and 316-2 respectively. Illustratively, a top surface 318 of the wick 238 abuts the two ends 316-1 and 316-2 of the ring separator 240 and the gas barrier 242 assembled to the reference electrode 226. Further, a bottom surface 320 of the wick 238 abuts to the counter electrode 228.

In accordance with said example embodiments, two portions 321 and 322 respectively of the counter electrode 228 illustrates abutment of various components below the counter electrode 228 with a bottom surface of the counter electrode 228. For instance, referring to the portion 321, a bottom surface 319 of the counter electrode 228 abuts with the central vent membrane 236 and the carbon cloth 234 that can be positioned above the support table 230. Referring to the portion 322, the bottom surface 319 of the counter electrode 228 abuts with the vent separators 232 that are seated into an end the support table 230. As illustrated from the sectional view the support table 230 can be further engaged into the epoxy 218 and further into the body molding 210. The sensor assembly of the EGS 200 can be further connected to a substrate of the PCB 206 via one or more PCB retaining features 223.

In accordance with various example embodiments described herein, a section of the EGS 200 can include a venting assembly 350 that can be adapted to provide a passage for venting various gases generated at the counter electrode 228, out from a body of the EGS 200. In this aspect, in some example embodiments, during an operation of the EGS 200 that involves an electrochemical reaction at the sensing electrode 222, at the counter electrode 228 oxygen may be generated. As described previously, these gases generated at the counter electrode 228 are desired to be vented out from the body molding 210 of the EGS 200, for increasing operational performance of the EGS 200 and also for preventing overall degradation to various electrical components of the EGS 200. The venting assembly 350 can include, a vent conduit 324 and the vent membrane 252 positioned over the extended portion 228-1 of the counter electrode 228. In some embodiments, the extended portion 228-1 of the counter electrode 228, via the vent membrane 252 and further via the vent conduit 324 can provide a passage to the gases, like oxygen, generated at the counter electrode 228 to be released out from the EGS 200. Further details of the venting assembly 350 are described in reference to FIGS. 4 and 5 described hereinafter.

Figure 4:
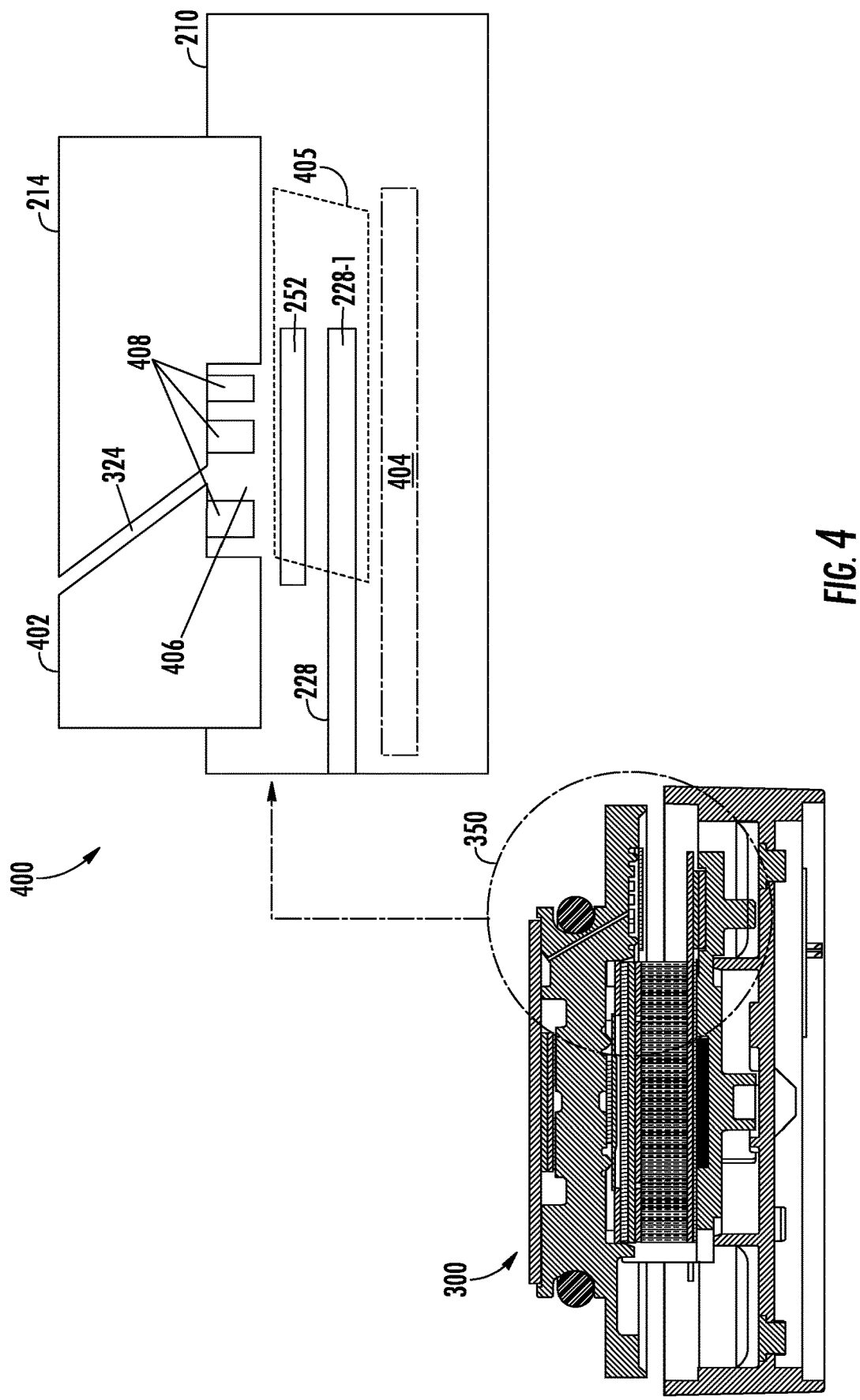
FIG. 4 schematically depicts a block diagram representing various components of a venting system of an electrochemical gas sensor, in accordance with some example embodiments described herein.

FIG. 4 schematically depicts a block diagram representing various components of a venting system 400 of an electrochemical gas sensor, (for example, the EGS 100, 200, 300 described in FIGS. 1-3 respectively). In accordance with some example embodiments described herein, the venting system 400 (also referred interchangeably as a venting assembly throughout the description) includes components, but not limited to, (a) the vent membrane 252, (b) the vent conduit 324, and (c) the extended portion 228-1 of the counter electrode 228. In some embodiments, the venting system 400 optionally also includes, a compression aid 404 such as, the vent separators 232 supporting the counter electrode 228 in the EGS (100, 200, 300) assembly. In accordance with said example embodiments, the venting system 400 can be operable to provide a passage to one or more gases, for example oxygen, that can be generated at the counter electrode 228, during an operation of the EGS (100, 200, 300) that involves an electrochemical reaction at one or more electrodes of the EGS (100, 200, 300). Additionally, and/or alternatively, the venting system 400 may also be operable to provide passage to one or more gases that may be present inside the EGS and are to be vented out from the EGS to maintain pressure differential inside and outside of the EGS 100, 200, 300. In this regard, in an example embodiment, the venting system is operable to provide a passage for gas inside the EGS (100, 200, 300) to be vented based on a pressure differential between inside and outside of the EGS (100, 200, 300). For instance, the venting system can be operable such that the pressure differential between inside and outside of the electrochemical oxygen sensor can be less than about 100%, less than about 75%, less than about 50%, less than about 25%, less than about 10%, less than about 5%, or less than about 1%, inclusive of all values and ranges therebetween.

In accordance with various example embodiments described herein, a gas may flow through the counter electrode 228 via the passage defined via the extended portion 228-1 of the counter electrode 228 to the vent membrane 252, and further via the vent membrane 252 to the vent conduit 324. To this extent, in accordance with some example embodiments, in the EGS (100, 200, 300) assembly the vent membrane 252 can be positioned over the counter electrode 228 so that, at least a portion 405 of the vent membrane 252 overlaps with the extended portion 228-1 of the counter electrode 228, thereby defining a part of the passage for the gas to flow from a surface of the counter electrode 228, via the extended portion 228-1, and further through a porous substrate of the vent membrane 252. In this regard, in accordance with some example embodiments described herein, in the assembly of the EGS (100, 200, 300), the vent membrane 252 may be in fluidic communication with the counter electrode 228 of the EGS (100, 200, 300).

Further, in some embodiments, the passage for gas flow can extend from a top surface of the vent membrane 252 to one end of the vent conduit 324. In some example embodiments, the venting system 400 includes the cavity 406 defined based on interstitial spacing between an internal surface of one or more solid features 408 defined at the sensor cap 214 and a portion of the vent membrane 252. Further details of the one or more solid features 408 defined on the sensor cap 214 are described in FIGS. 5 and 6 respectively. In accordance with various example embodiments described herein, the cavity 406 can be operable to accumulate a gas flow, as the gas gets released out through the vent membrane 252, and before the gas vents out of the body molding 210 of the EGS 200 through the vent conduit 324, thereby maintaining a pressure differential inside and outside of the EGS (100, 200, 300).

In accordance with some example embodiments, a substrate of the vent membrane 252 may be made up of a polymer with a defined porosity and a water ingress pressure within a defined range. To this extent, the porosity defined for the vent membrane 252 may supports passage of the gases generated at the counter electrode 228, however restricts ingress and egress of water into through its substrate. For instance, in some example embodiments, the substrate of the vent membrane 252 may be of a thickness within a range from about 0.12 mm to about 0.17 mm, or more preferably within a range from about 0.145 mm to about 0.165 mm. In some example embodiments, the vent membrane 252 may be of a thickness greater than 0.10 mm, 0.12 mm, 0.14 mm, 0.17 mm, 0.18 mm, inclusive of all values and ranges therebetween. In some other example embodiments, the substrate vent membrane 252 may be of thickness less than 0.10 mm, 0.12 mm, 0.145 mm, 0.165 mm, and 0.175 mm, inclusive of all values and ranges therebetween. Further, in accordance with said example embodiments, the vent membrane 252 may support a water ingress pressure within a range from about 4000 mbar to about 5200 mbar, or more preferably within a range from about 4200 mbar to about 5000 mbar. In some example embodiments, the vent membrane 252 may support a water ingress pressure that may be greater than 4800 mbar, 5000 mbar, 5200 mbar, 5300 mbar, inclusive of all values and ranges therebetween. In some other example embodiments, the vent membrane 252 may support a water ingress pressure that may be lesser than 3800 mbar, 3900 mbar, 3800 mbar, 4000 mbar, 4200 mbar, 4300 mbar, inclusive of all values and ranges therebetween. Furthermore, in accordance with some example embodiments, a Gurley number of the vent membrane 252 may be within a range from about 2000s to about 3500s, or more preferably within a range from about 2100s to about 3200s. In some example embodiments, a Gurley number of the vent membrane 252 may be greater than 3000s, 3100s, 3200s, 3400s, 3500s, 3600s, inclusive of all values and ranges therebetween. Further, in some example embodiments, a Gurley number of the vent membrane 252 may be lesser than 1900s, 2000s, 2100s, 2200s, 2300s, inclusive of all values and ranges therebetween.

Further, in accordance with example embodiments, the extended portion 228-1 of the counter electrode 228 may include a first synthetic polymer having a first porosity and the vent membrane 252 may include a second synthetic polymer having a second porosity. In accordance with some example embodiments, the second porosity associated with the vent membrane 252 may be lower than the first porosity associated with the extended portion 228-1 such that, a flow of a gas generated at a surface of the counter electrode 228 is initially faster as the gas flows through the extended portion 228-1 and gradually slows down as the gases are passed through into the vent conduit 324 through the vent membrane 252.

Figure 5:
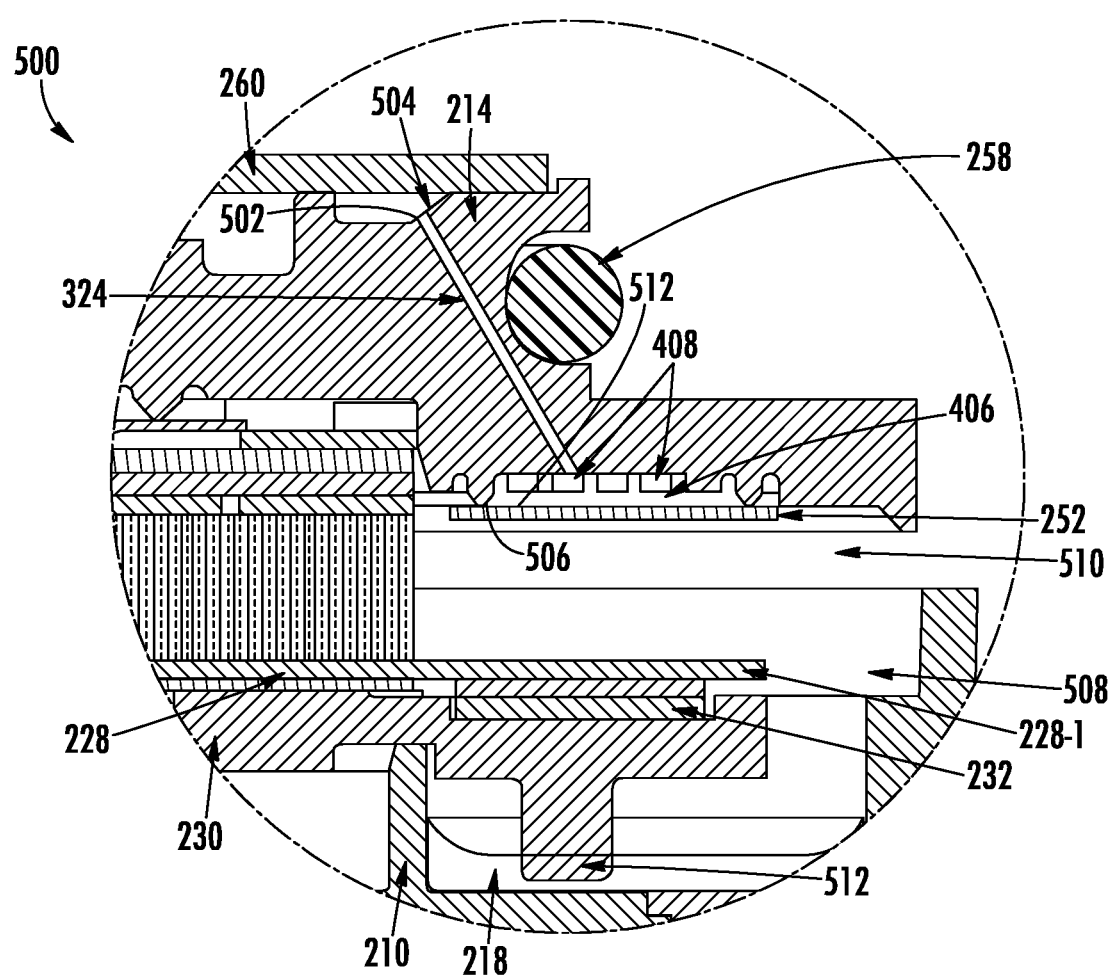
FIG. 5 schematically depicts an enlarged section illustrating the internal structure of the electrochemical gas sensor having a vent at a counter electrode of the electrochemical gas sensor, in accordance with some example embodiments described herein.

Referring to FIG. 5, an enlarged sectional view of the EGS (100, 200, 300), illustrating a portion 500, that can include the venting assembly 350 is illustrated. Illustratively, the sensor cap 214 from one end 502 of its outer surface 504 can define the vent conduit 324 that can extend through the substrate of the sensor cap 214 up to a portion of an internal surface 506 of the sensor cap 214 that corresponds to a part of the vent membrane 252. In this aspect, the vent conduit 324 can be of a defined aperture and can be defined at the one end 502 of the sensor cap 214. In accordance with said example embodiments, the vent conduit 324 may be dimensioned and configured such that the gas may vent through the passage defined by a channel of the vent conduit 324, and further out from the EGS (100, 200, 300) through the aperture at the one end 502 of the sensor cap 214. In some example embodiments, the aperture at the one end 502 of the sensor cap 214 may be defined such that, while the vent conduit 324 facilitates an egress of the gas out, however, at least one of the vent membrane 252 and the vent conduit 324, prevents any water flow or moisture may be prevented from entering the EGS (100, 200, 300) at least partially through capillary forces present at the vent conduit 324.

In accordance with various example embodiments described herein, the sensor cap 214 may be positioned at a top end of the EGS (100, 200, 300). In some embodiments, the venting system 350 can be operable to facilitate a flow of the gas generated at the counter electrode out from the body molding 210 of the EGS (100, 200, 300), via an opening of the aperture and from the one end 502 at top of the EGS (100, 200, 300). As gas vents out from the top end of the EGS (100, 200, 300) any chances of various electrical components at the PCB 206 of the EGS (100, 200, 300) being exposed to the generated gas and further condensation of such components can be avoided.

In accordance with some example embodiments described herein, in an example operation of the EGS 200, oxygen may be generated at the counter electrode 228 to compensate for a reaction of at the sensing electrode 222 of the EGS (100, 200, 300). In this regard, the oxygen generated at the counter electrode 228 may flow via a membrane of the extended portion 228-1, into an electrolyte reservoir 508 of the EGS (100, 200, 300), and further up to the vent membrane 252, via a path 510, where it gets diffused via various pores on the vent membrane 252 into the cavity 406 that can be defined between the interstitial spaces of the one or more solid features 408 and a top surface 512 of the vent membrane 252. In this aspect, the cavity 406 of the EGS (100, 200, 300) may be of a defined volume that supports accumulation of the oxygen before it eventually vents out of the EGS (100, 200, 300) through the vent conduit 324. In some example embodiments, the one or more solid features 408 defining the cavity 406 can be defined by an array of pillar shaped structures that are molded within a substrate of the sensor cap 214. According to various example embodiments described herein, the cavity 406 defined by the one or more solid features 408, can be dimensioned and configured to prevent a deformation of the vent membrane 252 during use of the EGS (100, 200, 300) with the sensor cap 214.

In various known electrochemical gas sensors, membranes supporting the ingress or egress of gases within sensor body, usually experience compressive forces due to assembling of various components of the electrochemical gas sensors, and also due to pressure differential inside and outside of the assembly of the electrochemical gas sensors. In such cases, often these membrane gets stick to other components of the sensor which is undesired. In accordance with various example embodiments described herein, the cavity 406, firstly can prevent the deformation of the vent membrane 252. For instance, the cavity 406 defined by the one or more solid features 408, can provide a pressure relief within the EGS (100, 200, 300) and can control compressive pressure on the vent membrane 252, by accumulating gases in the cavity 406, before eventually venting out the gases. To this end, the gases can be accumulated in the cavity 406 such that, the gases remain chemically inactive and are not exposed to any electrode of the EGS (100, 200, 300) before eventually being vented out from the EGS (100, 200, 300). Secondly, the cavity 406 can provide sufficient space between the top surface 512 of the vent membrane 252 and an internal surface 506 of the sensor cap 214 that can prevent any sticking of the vent membrane 252 with the sensor cap 214.

Figure 6:
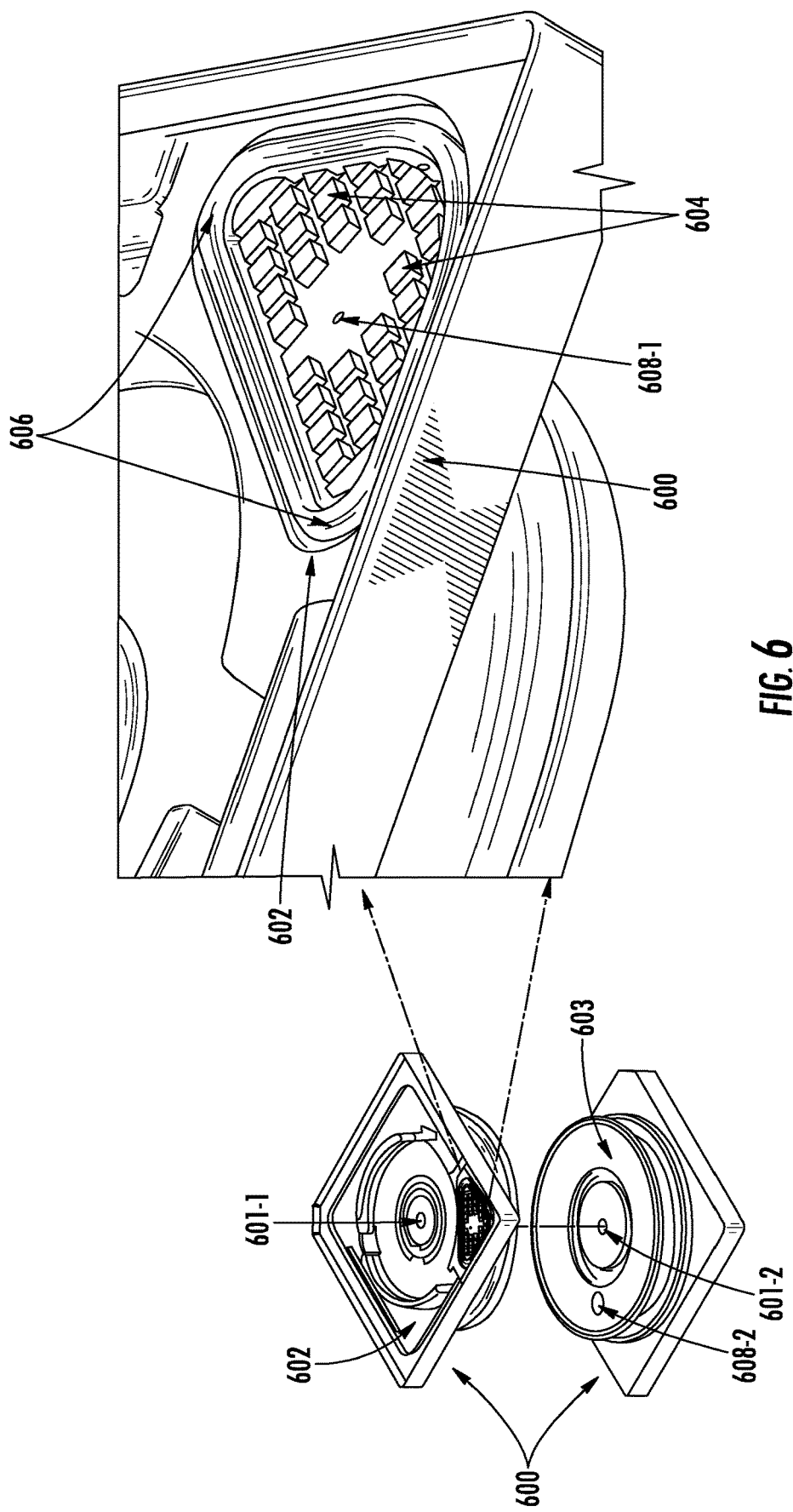
FIG. 6 illustrates a perspective view of a portion of the electrochemical gas sensor having one or more solid features, in accordance with an embodiment described herein.

FIG. 6 illustrates a perspective view of a portion of an electrochemical gas sensor having one or more solid features, in accordance with some example embodiments described herein. In some embodiments, a sensor cap 600 of the electrochemical gas sensor (for example the EGS 100, 200, 300) can include a top surface 602 and a bottom surface 603. As illustrated, the one or more solid features 604 can be defined on a portion 606 of the top surface 602 of the sensor cap 600. In some example embodiments, the one or more solid features 604 can be defined by an array of pillar shaped molds in a substrate of the sensor cap 600 that can protrude outwardly from the top surface 602 of the sensor cap 600. The top surface 602 also can include a capillary opening first end 601-1 and a vent conduit first end 608-1. The bottom surface 603 can include a capillary opening second end 601-2 and a vent conduit second end 608-2. In some example embodiments, a capillary may be defined as a channel that extends from the capillary opening first end 601-1, through falls via the substrate of the sensor cap 600, and further up to the capillary opening second end 601-2. In some examples, the capillary described herein may correspond to the capillary 310 as described in FIG. 3. In some example embodiments, the capillary 601 may be dimensioned and configured to provide an ingress of a target gas inside the EGS (100, 200, 300), in an instance, when the sensor cap 600 can be assembled in the electrochemical gas sensor. Further, the vent conduit first end 608-1 and the vent conduit second end 608-2 may defined a vent conduit (like the vent conduit 324 as described in FIGS. 3-5 respectively). In this aspect, the vent conduit may be operable to facilitate venting out of various gases inside the EGS (100, 200, 300), from the top surface 602 of the sensor cap 600, via the vent conduit first end 608-1.

In accordance with some example embodiments, the sensor cap 600 described herein may correspond to the sensor cap 214 and the one or more solid features 604 correspond to the one or more solid features 408, as described in FIGS. 1-5 respectively. To this extent, referring to the FIGS. 1-6, the one or more solid features 604 may be defined, but not limited to, in form of an array of pillars moulded into the sensor cap 600 that raises the vent membrane 252 (shown in FIGS. 2-5 respectively) above the vent conduit 324 to prevent blocking of the vent membrane 252 and to ensure adequate available area for the vent membrane 252 to minimise resistance to air flow through its substrate.

Figure 7:
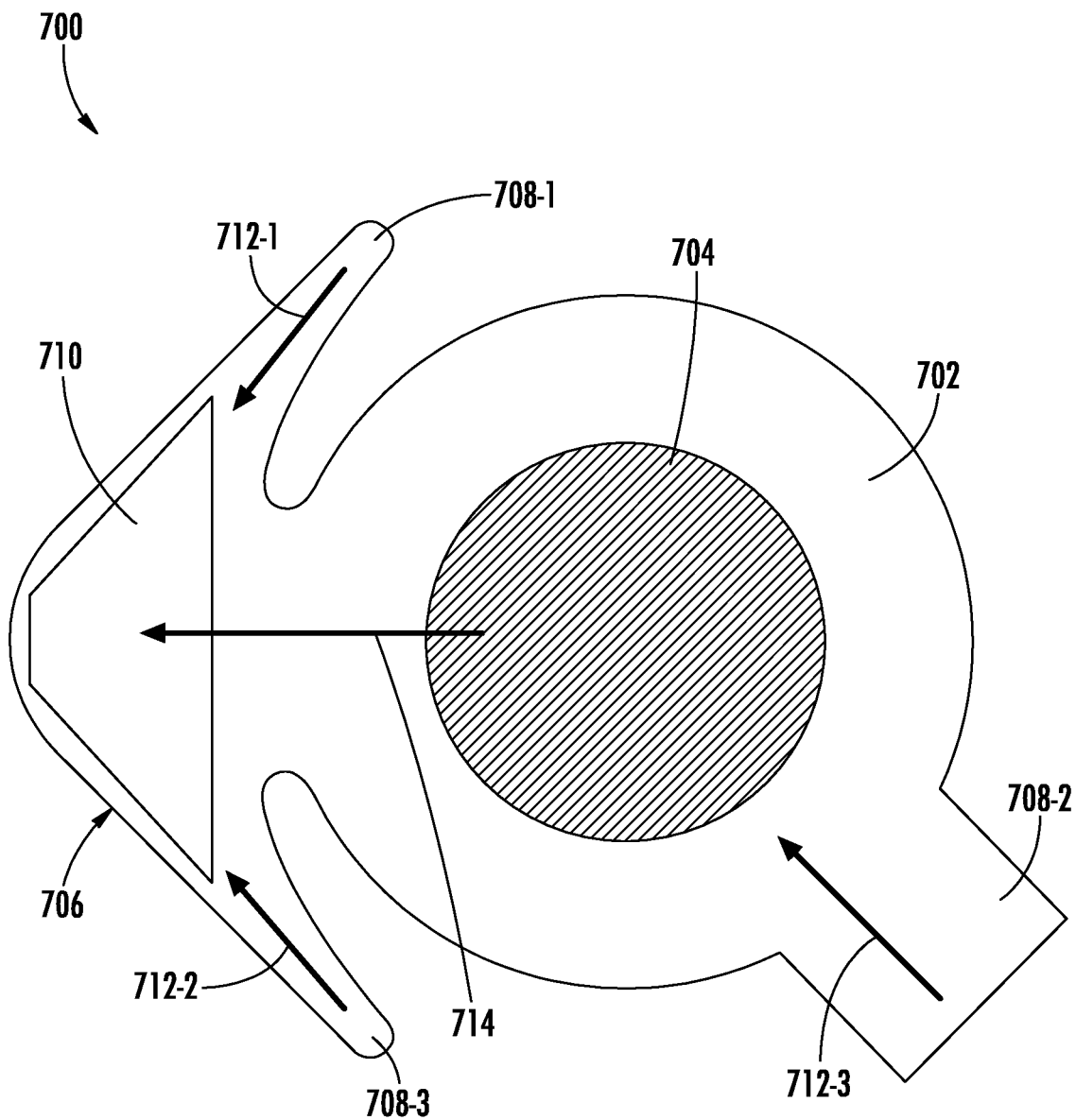
FIG. 7 schematically illustrates a counter electrode of the electrochemical gas sensor, in accordance with some example embodiments described herein.

FIG. 7 schematically illustrates a counter electrode 700 of an EGS, in accordance with some example embodiments described herein. In some embodiments, the counter electrode 700 can comprise a counter electrode substrate 702 over which a counter electrode catalyst 704 may be printed. In some example embodiments, the counter electrode substrate 702 can be of a circular shape and can be dimensioned to be fitted into a support table in the electrochemical gas sensor. In some example embodiments, the counter electrode 700 may be of a shape complimentary to one or more perforations that may be present on the support table such that, the counter electrode 700 may be recessed into the support table of the EGS. According to various example embodiments described herein, the counter electrode 700 includes an extended portion 706 that extends out from one end through a periphery of the counter electrode substrate 702.

In some example embodiments, the counter electrode substrate 702 including the extended portion 706 may be designed to meet various parameters for instance, a thickness, a water ingress pressure, an airflow, a Gurley number, and a porosity that are within defined ranges. The counter electrode substrate 702, in accordance with various example embodiments described herein, may be made of a synthetic polymer or a porous material such as, Polytetrafluoroethylene (PTFE) comprising pores that supports passage of gases present at the counter electrode 700.

According to some example embodiments described herein, the thickness of the counter electrode substrate 702 of the counter electrode 700 may be within a range from about 0.15 mm to about 0.21 mm, or more preferably within a range from about 0.17 mm to about 0.21 mm. For instance, in some example embodiments, the counter electrode substrate 702 of the counter electrode 700 may be of a thickness greater than 0.18 mm, 0.19 mm, 0.20 mm, 0.21 mm, 0.22 mm, inclusive of all values and ranges therebetween. In some example embodiments, the counter electrode substrate 702 may be of a thickness less than 0.12 mm, 0.13 mm, 0.14 mm, 0.15 mm, 0.16 mm, 0.17 mm, 0.18 mm, inclusive of all values and ranges therebetween.

Further, in accordance with said example embodiments, the counter electrode substrate 702 may be adapted to withhold a water ingress pressure within a range from about 300 mbar to about 1100 mbar, or more preferably within a range from about 830 mbar to about 1030 mbar, or even more preferably within a range from about 310 mbar to about 520 mbar. In some example embodiments, the counter electrode substrate 702 may be adapted to withhold a water ingress pressure greater than 500 mbar, 520 mbar, 530 mbar, 1000 mbar, 1030 mbar, 1100 mbar, 1150 mbar, inclusive of all values and ranges therebetween. In some other example embodiments, the counter electrode substrate 702 may be adapted to withhold a water ingress pressure less than 250 mbar, 300 mbar, 310 mbar, 700 mbar, 830 mbar, 850 mbar, inclusive of all values and ranges therebetween.

In an example embodiment, the counter electrode substrate 702 may support an airflow at a pressure differential 70 mbar within a range from about 3.2 liters/hr/cm$^2$ to about 11.8 liters/hr/cm$^2$, or more preferably within a range from about 6.8 liters/hr/cm$^2$ to about 11.4 liters/hr/cm$^2$. For instance, in some example embodiments, the counter electrode substrate 702 at a pressure differential 70 mbar may support an airflow greater than 11.0 liters/hr/cm$^2$, 11.2 liters/hr/cm$^2$, 11.4 liters/hr/cm$^2$, 11.6 liters/hr/cm$^2$, 11.8 liters/hr/cm$^2$, 12.0 liters/hr/cm$^2$, inclusive of all values and ranges therebetween. In some example embodiments, the counter electrode substrate 702 at a pressure differential 70 mbar may support an airflow less than 3.0 liters/hr/cm$^2$, 3.2 liters/hr/cm$^2$, 3.5 liters/hr/cm$^2$, 4.0 liters/hr/cm$^2$, 4.0 liters/hr/cm$^2$, 6.4 liters/hr/cm$^2$, 6.8 liters/hr/cm$^2$, 7.0 liters/hr/cm$^2$, inclusive of all values and ranges therebetween. According to some example embodiments, the counter electrode substrate 702 may be of a porosity within a range from about 20% to about 50% of the substrate, or more preferably within a range from about 25% to about 35%, or even more preferably within a range from about 40% to about 45% of the substrate. In some example embodiments, the counter electrode substrate 702 may be of a porosity greater than 30%, 35%, 40%, 45%, 50%, 55%, inclusive of all values and ranges therebetween. In some example embodiments, the counter electrode substrate 702 may be of a porosity less than 18%, 20%, 25%, 30%, 40%, 45%, 48%, inclusive of all values and ranges therebetween.

In some embodiments, the counter electrode 700 can also include one or more breather tabs 708-1, 708-2, and 708-3 that can be defined respectively about a periphery of the counter electrode 700. In some example embodiments, the one or more breather tabs 708-1, 708-2, and 708-3 may be dimensioned and may be configured to support a passage of air or gases inside the electrochemical gas sensor for pressure relief. For instance, in some example embodiments, the one or more breather tabs 708-1, 708-2, and 708-3 may be adapted to allow pressure equilibration from a sensor reservoir to the vent assembly. In some embodiments, the counter electrode 700 can include multiple such tabs to ensure that at least one tab from among the one or more breather tabs 708-1, 708-2, and 708-3 would remain in contact with air space within a body molding of the electrochemical gas sensor regardless of orientation of the electrochemical gas sensor. In some example embodiments, the one or more breather tabs 708-1, 708-2, and 708-3 may be made of highly porous synthetic polymer such as, a PTFE membrane having a low Gurley number. In some embodiments, in the assembly of an electrochemical gas sensor, locations corresponding to the one or more breather tabs 708-1, 708-2, and 708-3 are prone to high oxidizing and reactive environment. In accordance with some example embodiments, the one or more breather tabs 708-1, 708-2, and 708-3 may be made of an inert material such as platinum. In some example embodiments, the one or more breather tabs 708-1, 708-2, and 708-3 may comprise or be made of a microporous membrane material such as Mupor PTFE.

In accordance with various example embodiments described herein, upon assembling the counter electrode 700, and other associated components of the electrochemical gas sensor, a portion of a vent membrane in the venting assembly of the electrochemical gas sensor, can be positioned over the extended portion 228-1 of the counter electrode, represented as vent membrane overlap 710 in FIG. 7. In some example embodiments, any gas (generated at the counter electrode due to an electrochemical reaction inside an electrochemical cell of the electrochemical gas sensor) may flow through interstitial spacing between the portion of the vent membrane overlap 710 and the extended portion 706 of the counter electrode 700, in a direction 714. Further, additionally, and/or alternatively, any air present in a reservoir below the counter electrode 700 and inside the electrochemical gas sensor, and may flow through the one or more breather tabs 708-1, 708-2, and 708-3 in directions 712-1, 712-2, and 712-3 respectively, towards the extended portion 706 of the counter electrode 700. In some example embodiments, the air flow through the one or more breather tabs 708-1, 708-2, and 708-3 may be to maintain a pressure equilibrium inside and outside the body of the electrochemical gas sensor. Accordingly, the flow of the air may be in either direction, i.e. from the one or more breather tabs 708-1, 708-2, and 708-3 into the portion between the vent membrane and the extended portion 706 or vice versa, depending on pressure differential between inside and outside of the electrochemical gas sensor. In some example embodiments, the air flowing through the one or more breather tabs 708-1, 708-2, and 708-3 may be passed into interstitial spacing between the portion of the vent membrane overlap 710 and the extended portion 706 of the counter electrode 700, further upwards in the assembly of the electrochemical gas sensor, and furthermore to outside of the electrochemical gas sensor. In some example embodiments, oxygen generated at the counter electrode 700 may flow into the reservoir below the counter electrode 700 via the one or more breather tabs 708-1, 708-2, and 708-3, however, may be vented out eventually through the vent assembly of the electrochemical gas sensor.

In accordance with various example embodiments described herein, the EGS 100 may use various techniques and may additionally or alternatively include various components related to measuring concentration of one or more target gases as described in U.S. patent application Ser. No. 14/506,312, filed Oct. 3, 2014, entitled, "SUPPORT FOR ELECTRODE STACK & PROVISION FOR VENTING OF A GAS SENSOR USING AN INTERNALLY MOUNTED TABLE" and U.S. patent application Ser. No. 13/406,574 filed Feb. 28, 2012, entitled, "VENTED OXYGEN CELL," the entire contents of each of which are incorporated by reference herein.

In some example embodiments, certain ones of the operations herein may be modified or further amplified as described below. Moreover, in some embodiments additional optional operations may also be included. It should be appreciated that each of the modifications, optional additions or amplifications described herein may be included with the operations herein either alone or in combination with any others among the features described herein.

The foregoing method descriptions and the process flow diagrams are provided merely as illustrative examples and are not intended to require or imply that the steps of the various embodiments must be performed in the order presented. As will be appreciated by one of skill in the art, the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The hardware used to implement the various illustrative logics, logical blocks, modules, and circuits described in connection with the aspects disclosed herein may include a general purpose processor, a digital signal processor (DSP), a special-purpose processor such as an application specific integrated circuit (ASIC) or a field programmable gate array (FPGA), a programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, or in addition, some steps or methods may be performed by circuitry that is specific to a given function.

In one or more example embodiments, the functions described herein may be implemented by special-purpose hardware or a combination of hardware programmed by firmware or other software. In implementations relying on firmware or other software, the functions may be performed as a result of execution of one or more instructions stored on one or more non-transitory computer-readable media and/or one or more non-transitory processor-readable media. These instructions may be embodied by one or more processor-executable software modules that reside on the one or more non-transitory computer-readable or processor-readable storage media. Non-transitory computer-readable or processor-readable storage media may in this regard comprise any storage media that may be accessed by a computer or a processor. By way of example but not limitation, such non-transitory computer-readable or processor-readable media may include random access memory (RAM), read-only memory (ROM), electrically erasable programmable read-only memory (EEPROM), FLASH memory, disk storage, magnetic storage devices, or the like. Disk storage, as used herein, can include compact disc (CD), laser disc, optical disc, digital versatile disc (DVD), floppy disk, and Blu-ray disc™, or other storage devices that store data magnetically or optically with lasers. Combinations of the above types of media are also included within the scope of the terms non-transitory computer-readable and processor-readable media. Additionally, any combination of instructions stored on the one or more non-transitory processor-readable or computer-readable media may be referred to herein as a computer program product.

Many modifications and other embodiments of the inventions set forth herein will come to mind to one skilled in the art to which these inventions pertain having the benefit of teachings presented in the foregoing descriptions and the associated drawings. Although the figures only show certain components of the apparatus and systems described herein, it is understood that various other components may be used in conjunction with the supply management system. Therefore, it is to be understood that the inventions are not to be limited to the specific embodiments disclosed and that modifications and other embodiments are intended to be included within the scope of the appended claims. Moreover, the steps in the method described above may not necessarily occur in the order depicted in the accompanying diagrams, and in some cases one or more of the steps depicted may occur substantially simultaneously, or additional steps may be involved. Although specific terms are employed herein, they are used in a generic and descriptive sense only and not for purposes of limitation.

The invention claimed is:

1. An electrochemical gas sensor comprising:
a sensor cap comprising a plurality of solid features defined on a surface of the sensor cap;
a counter electrode configured to generate a gas; and
a vent assembly adapted to release at least a portion of the gas generated at the counter electrode out of the electrochemical gas sensor, wherein the vent assembly comprises a vent conduit and a vent membrane, wherein the plurality of solid features on the sensor cap define a cavity between an internal surface of the plurality of solid features and the vent membrane.

2. The electrochemical gas sensor of claim 1, wherein the cavity is operable to accumulate at least a portion of the gas released out through the vent membrane before the at least the portion of the gas vents out through the vent conduit.

3. The electrochemical gas sensor of claim 1, wherein the vent conduit is defined by an aperture from an outside surface of the sensor cap, through the sensor cap, and to a portion of an inner surface of the sensor cap corresponding to a portion of the vent membrane, and wherein the sensor cap is positioned at a top end of the electrochemical gas sensor.

4. The electrochemical gas sensor of claim 1, wherein the vent membrane is positioned over the counter electrode so that a portion of the vent membrane overlaps with an extended portion of the counter electrode, thereby defining a passage for oxygen generated at the counter electrode to flow through the extended portion into the vent membrane, and further vent out through the sensor cap of the electrochemical gas sensor, via the vent conduit, and wherein the extended portion of the counter electrode extends out from one end through a periphery of a substrate of the counter electrode.

5. The electrochemical gas sensor of claim 4, wherein the extended portion of the counter electrode comprises a first synthetic polymer having a first porosity.

6. The electrochemical gas sensor of claim 5, wherein the vent membrane comprises a second synthetic polymer having a second porosity lower than the first porosity and a water ingress pressure within a defined range.

7. A gas sensor cap for an electrochemical gas sensor comprising:
a housing, wherein a portion of the housing comprises an aperture through at least one surface of the housing, the aperture dimensioned and configured to prevent water ingress to the electrochemical gas sensor and allow gas egress from the electrochemical gas sensor; and a plurality of solid features disposed on the at least one surface of the portion of the housing wherein a vent membrane is adapted to be heat sealed at a portion of the gas sensor cap, and wherein the plurality of solid features defines a cavity between an internal surface of a plurality of pillar shaped moldings and a portion of the vent membrane.

8. The gas sensor cap of claim 7, wherein the gas sensor cap is adapted to be engaged at a top end of the electrochemical gas sensor, and wherein the aperture is in fluidic communication with a portion of the electrochemical gas sensor comprising a counter electrode.

9. The gas sensor cap of claim 8, wherein upon engagement with the electrochemical gas sensor, the gas sensor cap is adapted to vent out the gas generated inside the electrochemical gas sensor through a top end of the gas sensor cap.

10. The gas sensor cap of claim 7, wherein the vent membrane comprises a synthetic polymer having a porosity within a first defined range and a water ingress pressure within a second defined range.

11. The gas sensor cap of claim 7, wherein the cavity is operable to accumulate at least a portion of the gas generated at a counter electrode of the electrochemical gas sensor and released out through the vent membrane before the gas vents out through a vent conduit, and wherein the vent membrane of the gas sensor cap is in fluidic communication with the counter electrode of the electrochemical gas sensor.

12. An electrochemical oxygen sensor comprising:
a sensor cap comprising a plurality of pillar shaped moldings on a top surface of the sensor cap;
a counter electrode operable to generate oxygen;
a venting system comprising:
a vent membrane dimensioned and configured to have a porosity,
a vent conduit defined by an aperture in the sensor cap that is dimensioned and configured such that gas can vent from the electrochemical oxygen sensor and water is prevented from entering the electrochemical oxygen sensor at least partially through capillary forces, and
an extended portion of the counter electrode, wherein the extended portion of the counter electrode extends out from one end through a periphery of a substrate of the counter electrode.

13. The electrochemical oxygen sensor of claim 12, wherein the venting system is operable to provide a passage to the oxygen generated at the counter electrode via the extended portion of the counter electrode to the vent membrane and further via the vent conduit through the top surface of the sensor cap.

14. The electrochemical oxygen sensor of claim 12, wherein the sensor cap is positioned at a top end of the electrochemical oxygen sensor, and wherein the vent conduit comprises a channel defined from an open end at the top surface of the sensor cap, through the sensor cap, to one another end at a bottom surface of the sensor cap and further to a portion of the vent membrane.

15. The electrochemical oxygen sensor of claim 14, wherein the extended portion of the counter electrode comprises a first synthetic polymer having a first porosity within a defined first range.

16. The electrochemical oxygen sensor of claim 15, wherein the vent membrane comprises a second synthetic polymer having a second porosity within a defined second range and a water ingress pressure within a defined range.

17. The electrochemical oxygen sensor of claim 12, wherein the vent membrane is positioned over the counter electrode so that a portion of the vent membrane overlaps with the extended portion of the counter electrode, thereby defining a passage for the oxygen generated at the counter electrode to flow through the extended portion into the vent membrane and vent out through a top end of the electrochemical oxygen sensor via an opening of the vent conduit.

18. The electrochemical oxygen sensor of claim 12, wherein the plurality of pillar shaped moldings on the sensor cap defines a cavity between an internal surface of the plurality of pillar shaped moldings and the vent membrane.

19. The electrochemical oxygen sensor of claim 18, wherein the cavity is operable to accumulate the oxygen released out through the vent membrane before the oxygen vents out through the vent conduit.

* * * * *